US012562272B2

(12) United States Patent
Sommer et al.

(10) Patent No.: US 12,562,272 B2
(45) Date of Patent: Feb. 24, 2026

(54) PORTABLE TELEMEDICINE APPARATUS

(71) Applicants: Darren J. Sommer, Indian Shores, FL (US); Dennis A. Kopp, Little Rock, AR (US)

(72) Inventors: Darren J. Sommer, Indian Shores, FL (US); Dennis A. Kopp, Little Rock, AR (US)

( * ) Notice: Subject to any disclaimer, the term of this patent is extended or adjusted under 35 U.S.C. 154(b) by 469 days.

(21) Appl. No.: 17/962,805

(22) Filed: Oct. 10, 2022

(65) Prior Publication Data

US 2024/0120086 A1      Apr. 11, 2024

(51) Int. Cl.
*G16H 40/67* (2018.01)
*G16H 80/00* (2018.01)
*H04N 7/14* (2006.01)

(52) U.S. Cl.
CPC ............. *G16H 40/67* (2018.01); *G16H 80/00* (2018.01); *H04N 7/142* (2013.01)

(58) Field of Classification Search
CPC ......... G16H 40/67; G16H 80/00; H04N 7/142
See application file for complete search history.

(56) References Cited

U.S. PATENT DOCUMENTS

| | | | | |
|---|---|---|---|---|
| 6,011,699 A * | 1/2000 | Murray | ............... | H04M 1/0216 |
| | | | | 379/433.05 |
| 9,485,557 B2 * | 11/2016 | Wilcox | ................. | H04R 7/045 |

| | | | | |
|---|---|---|---|---|
| 10,254,863 B2 * | 4/2019 | Shin | ........................ | G06F 3/041 |
| 10,357,156 B2 | 7/2019 | Sommer et al. | | |
| 11,181,227 B1 * | 11/2021 | Pontecorvo | .......... | F16M 11/041 |
| 11,388,966 B2 * | 7/2022 | Balmer | .................. | A45C 15/00 |
| 12,055,980 B2 * | 8/2024 | Jun | ........................ | H04N 23/69 |
| 12,138,041 B1 * | 11/2024 | Filipovic | ......... | H04M 1/724092 |
| 2006/0208441 A1 * | 9/2006 | Lin | ........................ | G03B 17/02 |
| | | | | 280/47.131 |
| 2008/0076471 A1 * | 3/2008 | Yuki | ...................... | H04N 7/142 |
| | | | | 348/E7.079 |
| 2008/0128505 A1 * | 6/2008 | Challa | .................. | G06K 7/1095 |
| | | | | 235/462.01 |
| 2010/0298032 A1 * | 11/2010 | Lee | ........................ | G06F 1/1616 |
| | | | | 345/173 |
| 2011/0084893 A1 * | 4/2011 | Lee | ......................... | G06F 3/016 |
| | | | | 345/6 |
| 2013/0077236 A1 * | 3/2013 | Becze | ................. | H04M 1/0266 |
| | | | | 361/679.56 |

(Continued)

*Primary Examiner* — Brian D Nash
(74) *Attorney, Agent, or Firm* — Jason H. Foster; Kremblas & Foster

(57) ABSTRACT

A portable communication apparatus including a wireless transceiver, a video display screen, a camera, a speaker and a microphone, some or all mounted in a case having a first portion and a second portion. The video display screen is mounted to the second portion with a viewable region of the video display screen facing away from the second portion. The first and second portions are pivotably attached to one another at a first case end. When the first and second portions are in a closed configuration they form an enclosed chamber in which the video display screen is positioned. When the first and second portions are in an opened configuration the first portion is positioned beneath the second portion. A hanger is mounted to the second portion near a second case end that is opposite the first case end to hang the case.

16 Claims, 17 Drawing Sheets

(56)        References Cited

U.S. PATENT DOCUMENTS

| | | | |
|---|---|---|---|
| 2014/0228082 A1* | 8/2014 | Morrow | H04B 1/3888 |
| | | | 455/575.8 |
| 2014/0380227 A1* | 12/2014 | Ng | G06F 1/1677 |
| | | | 715/778 |
| 2015/0077502 A1* | 3/2015 | Jordan | G06F 3/04883 |
| | | | 348/14.03 |
| 2017/0003711 A1* | 1/2017 | Rowley | F16B 11/006 |
| 2020/0120308 A1* | 4/2020 | McMillan | G06F 3/017 |

* cited by examiner

210

205

298

357

EXAM. CAMERA

EXAM. CAMERA

STETHOSCOPE

356

EXAM. CAMERA

84

83

PORTABLE TELEMEDICINE APPARATUS

BACKGROUND OF THE INVENTION

The invention relates generally to equipment used in communication of audio and/or video data, and more specifically to a first device that creates audio, video and possibly other data and transmits it to a second device in a location separate from the first device and the second device creates audio and video data and transmits it to the first device, thereby enabling patients and caretakers in different locations to communicate in real time.

The costs for medical patients to be transported to a medical facility and be examined by a medical professional can be significant. In some situations, such transport is impossible due to timing or physical obstacles. For example, if a soldier has a spinal injury, he is much more likely to survive and even completely recover if a neurologist treats him quickly. But a neurologist may not be available near the soldier. As another example, an athlete with a shoulder injury is more likely to recover fully if she is seen by an orthopedic specialist very soon after the injury. However, not all specialists are available to see patients as quickly as the patients need to be seen, for example due to transport time and availability of such specialists near the patient.

However, if a patient can be connected via a video and audio connection, a virtual diagnosis may be made so that a treatment may be implemented by those physically near to the patient, thereby avoiding the need for specialists to travel to the patient or vice versa. Many devices exist for conveying audio and video information between a patient and a medical professional, including U.S. Pat. No. 10,357,156 to Sommer et al., which is incorporated herein by reference. Such devices permit a doctor to view and converse with a patient in a remote location. Likewise, the patient is able to hear and see his or her doctor, despite being at a remote location from the doctor. Using the device described in the above-incorporated Sommer reference, the patient and the doctor might be on opposite sides of the world while a virtual examination and discussion with the patient is carried out using cameras, microphones and electronic displays that convey the audio and video signals over the Internet or some other form of electronic communication.

Some problems with the devices described in the above-incorporated Sommer patent are their size, weight, fragility and inability to convey communications when located in a remote location. This configuration works well in a doctor's office and a hospital setting, but the devices are not suitable for conditions that are physically unstable, such as ambulances and other transport settings.

Other current systems pose a substantial safety risk to the patient and medical attendants. For example, systems that are free to move around will do so when the vehicle transporting the patient and medical attendants makes sudden movements. Unsecured equipment in a helicopter or ambulance can become a moving object if the vehicle turns or loses elevation, creating a safety risk to the occupants of the vehicle.

The need exists for a device that readily can be used in various, physically unstable conditions without exposing those around it to added risk.

SUMMARY OF THE INVENTION

Disclosed herein is an improved portable communication apparatus including at least a wireless transceiver, a video display screen, a camera, a speaker and a microphone. The improvement comprises a case having at least a first portion and a second portion, wherein the video display screen is mounted to the second portion with a viewable region of the video display screen facing away from the second portion. Furthermore, the first and second portions are pivotally attached to one another at a first case end. Further still, when the first and second portions are in a closed configuration the first and second portions form an enclosed chamber in which the video display screen is positioned with the viewable region facing toward, and obstructed by, at least the first portion. Still further, when the first and second portions are in an opened configuration the first portion is positioned beneath the second portion and the video display screen, and the first portion is not obstructing the viewable region. The improvement also comprises a hanger mounted to the second portion near a second case end that is opposite the first case end, wherein the hanger is configured for hanging the case in at least the opened configuration.

In some embodiments, the improved portable communication apparatus further comprises at least one clamp attached to the second portion on a side of the second portion that is opposite the video display screen. In other embodiments, the improved portable communication apparatus further comprises at least one receptacle in the first portion configured for receiving instruments. In other embodiments, the improved portable communication apparatus further comprises a stand that is pivotally mounted to the case.

Disclosed herein is a combination human transport and a communication apparatus. The combination includes at least a wireless transceiver, a video display screen, a camera, a speaker and a microphone. The combination comprises a case having at least a first portion and a second portion, wherein the video display screen is mounted to the second portion with a viewable region of the video display screen facing away from the second portion, the first and second portions are pivotally attached to one another at a first case end, and the first portion is positioned beneath the second portion and the video display screen. The combination also comprises the second portion being mounted, near a second case end that is opposite the first case end, to the human transport.

In some embodiments, the combination further comprises at least one clamp mounted to the second portion on a side of the second portion that is opposite the video display screen. The at least one clamp is attached to the second portion and the human transport. In some embodiments, the combination in accordance with claim further comprises at least one receptacle in the first portion configured for receiving instruments. In some embodiments, the combination further comprises a stand that is pivotally mounted to the case. In some embodiments, the human transport further comprises a tubular member to which the second portion is mounted.

Disclosed herein is a method of communicating between first and second parties in separate locations. The method comprises disposing a patient on a human transport and mounting a communication apparatus to the human transport. The communication apparatus includes at least a wireless transceiver, a camera, a speaker, a microphone, and a video display screen that is mounted to a case having at least a first portion and a second portion. The video display screen is mounted to the second portion with a viewable region of the video display screen facing away from the second portion. The first and second portions are pivotally attached to one another at a first case end. The step of mounting comprises attaching to the human transport a hanger that is mounted to the case near a second case end that is opposite the first case end. The method further comprises disposing the first portion beneath the second portion and the video display screen. The method further comprises operating the communication apparatus, which includes at least the first party viewing live video of the second party transmitted to the transceiver and displayed on the video display screen, while simultaneously the case is mounted to the human transport, the first portion is disposed beneath the second portion and the video display screen, and video of the first party is captured by video that the transceiver transmits to the second party. In some embodiments, the step of mounting further comprises attaching at least one clamp, which is mounted to the second portion on a side of the second portion that is opposite the video display screen, to the human transport. In some embodiments, the method comprises removing at least one instrument from a receptacle in the first portion and connecting the instrument to the video display screen. In some embodiments the method further comprises pivoting a stand that is pivotably mounted to the case.

Figures 1, 2:
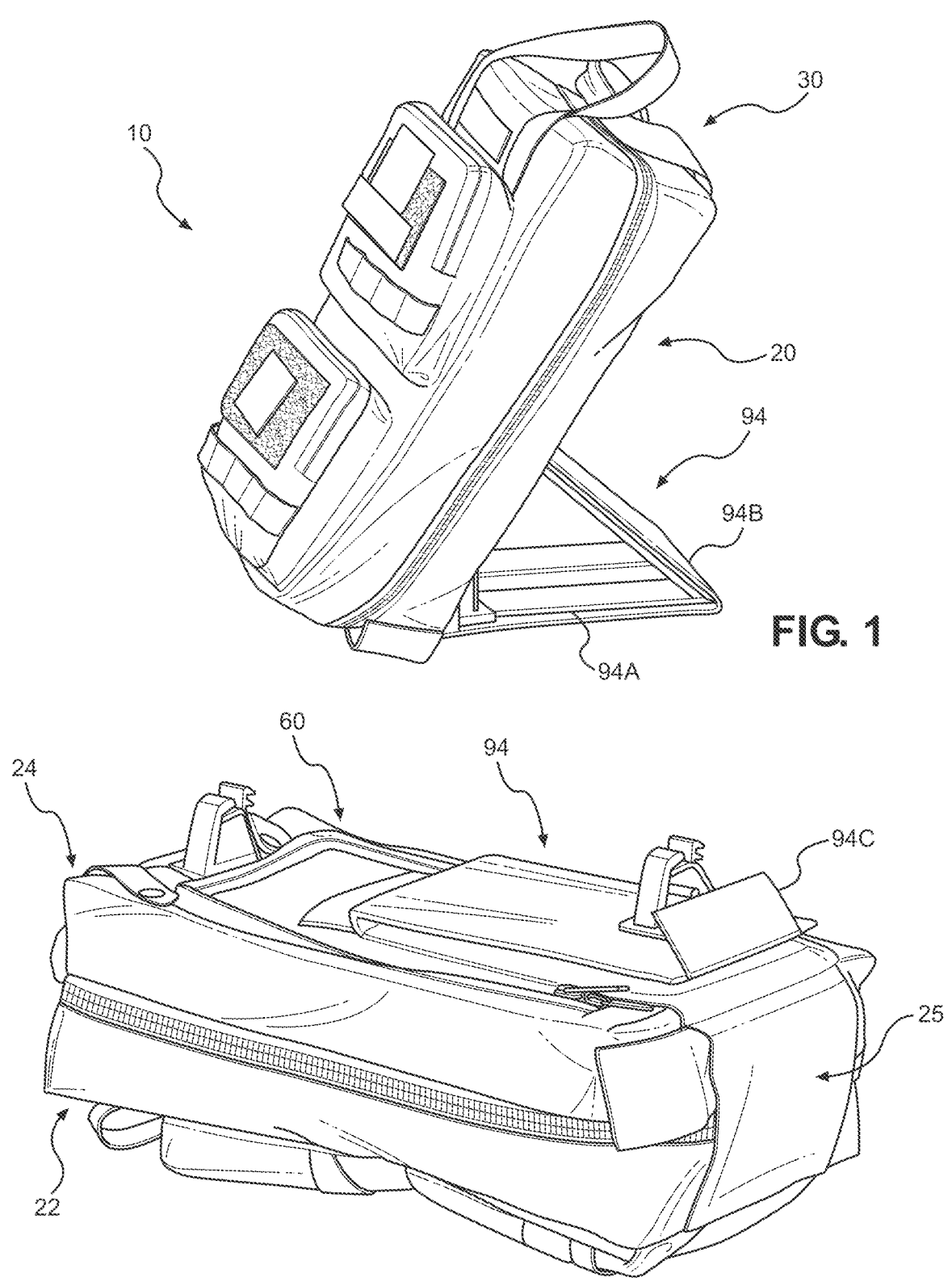
FIG. 1 is a view in perspective illustrating an embodiment of the present invention.
FIG. 2 is a view in perspective illustrating the embodiment of FIG. 1.

In describing the preferred embodiment of the invention which is illustrated in the drawings, specific terminology will be resorted to for the sake of clarity. However, it is not intended that the invention be limited to the specific term so selected and it is to be understood that each specific term includes all technical equivalents which operate in a similar manner to accomplish a similar purpose. For example, the word connected or terms similar thereto are often used. They are not limited to direct connection, but include connection through other elements where such connection is recognized as being equivalent by those skilled in the art.

DETAILED DESCRIPTION OF THE INVENTION

The apparatus 10 shown in FIG. 1 has a case 20 that may retain one or more communication components (not visible in FIG. 1) that together cooperate to serve as a portable communication apparatus. The components may include at least a wireless transceiver, a video display screen, a camera, a speaker and a microphone. While it is contemplated that the case 20 contains all components, some components may be contained in the case 20 and others may be separate from the case. For example, it is contemplated that the microphone and speakers may be components of a conventional headset that a human user wears during use of the apparatus 10 and that connects wirelessly or by wire to the transceiver contained in the case 20. Alternatively, the operator of the apparatus 10 may use a smart phone's camera, speaker, microphone and transceiver in conjunction with the video display screen contained in the case 20. Therefore, although all of the components of the communication apparatus are used, some components may be contained in or attached to the case, and others may be outside and/or unattached to the case. Furthermore, it is contemplated that other components may be used in addition to those described above, including a generally programmable computer and a power source, such as a battery, both of which may be integrated with the video display screen, such as in a tablet computer.

The wireless transceiver may be any device that sends and receives data wirelessly, using Bluetooth, WiFi and any other wireless technology. In the preferred embodiment, the wireless transceiver is a cellular telephone, such as a smartphone, which permits data transfer using conventional cellular networks. A person having ordinary skill will understand that there are many other such wireless transceivers that may be used as a substitute for the cellular telephone. These are not described exhaustively herein, because there are too many to describe and technology changes so rapidly in the area of communications that technology at the forefront of communications when this explanation is written are likely to be replaced soon thereafter by other technology. The absence of describing or naming a particular communication technology should not imply that such technology is not contemplated. Instead, it should be understood that a person of ordinary skill will recognize that various technologies that are currently in existence, as well as those that come into existence later, should be considered as substitutes for the communication technology described.

The video display screen 50 (FIG. 6) may be a component of a tablet computer or a smart phone, or it may be a computer monitor (e.g., LCD, LED, OLED or similar flat screen devices), or any other device that may substitute for these devices. This includes, but is not limited to, projectors and other visual image (hologram) presenting technology. In a preferred embodiment, the video display screen 50 is a display component of the tablet computer 52, which is a programmable computer. Such a tablet computer 52 may have other conventional components, such as a processor, a storage drive with an operating system, random access memory (RAM), connection ports (e.g., HDMI, USB, etc.), a microphone, a camera, and an onboard wireless transceiver (e.g., Bluetooth, WiFi, etc.) to communicate with a cellular telephone, or even a cellular telephone radio that can operate as a cellular telephone. The tablet computer 52 may be programmed with a user interface that cooperates with the video display screen, which is preferably a touch screen. A user may thus merely turn on the tablet computer and follow prompts that appear on the screen to operate the entire communication apparatus 10 with a graphical user interface.

The camera used with the present invention may be a video camera, such as a standalone web cam or similar device. Such a camera may be connected by wire or wirelessly to the tablet computer 52. As an alternative, the camera may be incorporated as an integral part of the tablet computer 52 of which the video display screen 50 is a component, as with the camera 54 and a sliding camera cover 53 shown in FIG. 6. Alternatively, the camera may be a camera on a smart phone that is operated by the operator of the apparatus 10. A still further alternative is that the camera may be a camera mounted to glasses (e.g., Google Glass) that the operator of the apparatus 10 wears on his or her face. Many other alternatives will be apparent from this description.

Figures 25, 26, 27:
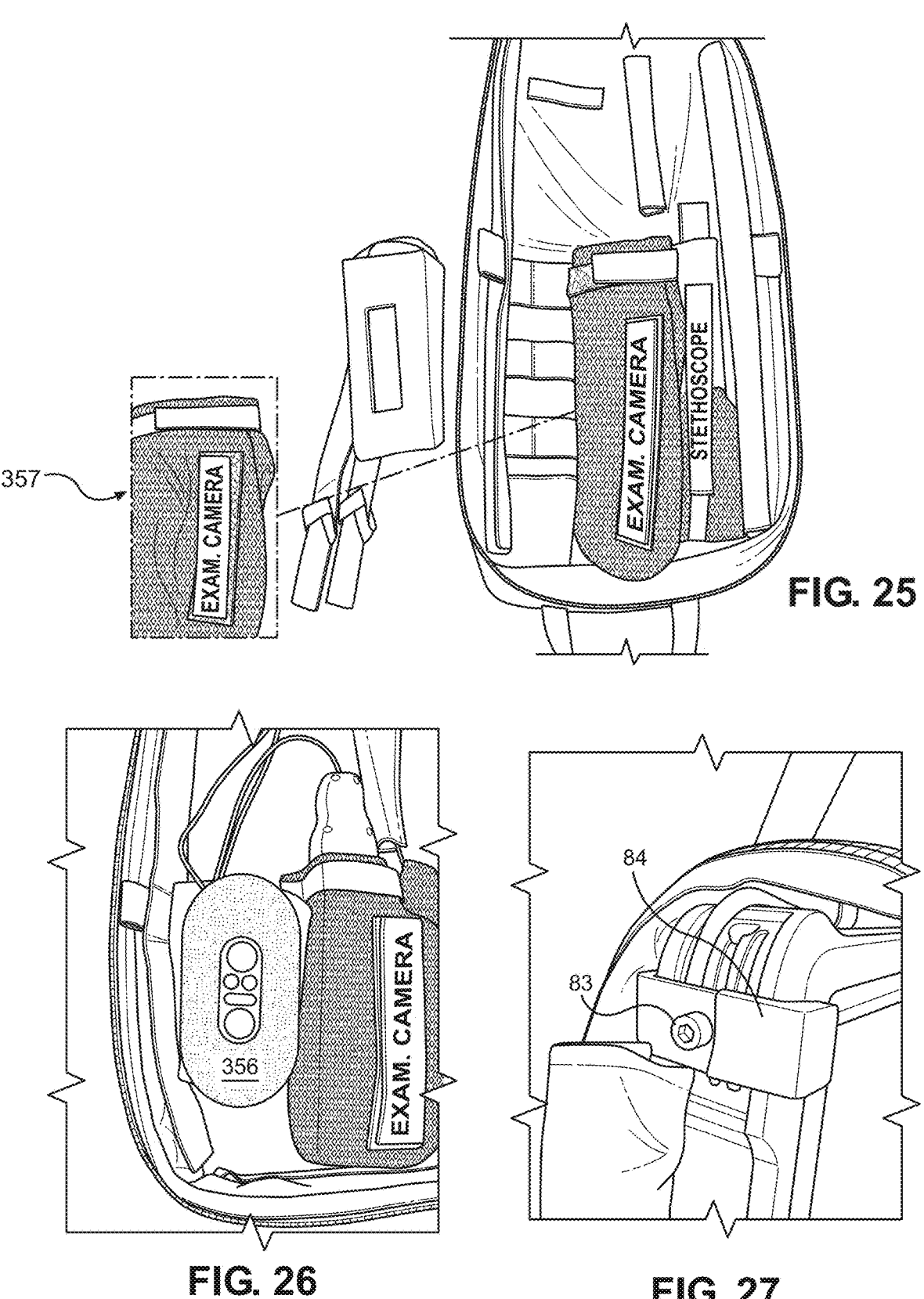
FIG. 25 is a front view illustrating a lower portion of an embodiment of the present invention.
FIG. 26 is a front view illustrating a lower portion of an embodiment of the present invention with an optional speaker mounted in an optional location.
FIG. 27 is a view in perspective illustrating a magnified attachment means for a tablet computer.

The speaker may be a standalone speaker connected by wire or wirelessly to the tablet computer. As shown in FIGS. 25-26, a standalone speaker device 356 may be attached to the case 20 directly using hooks and loops fasteners, or the speaker device 356 may be placed in a pouch 357 that is attached to the case 20 using hooks and loops fasteners as shown in FIG. 26. Of course, any suitable alternative fasteners can be substituted for hooks and loops fasteners. As an alternative, the speaker 56 (FIG. 7) may be incorporated into the tablet computer 52 of which the video display screen 50 is a component. Alternatively, the speaker may be an integrated speaker in a smart phone that is operated by the operator of the apparatus 10. A still further alternative is that the speaker may be wired or wireless ear buds connected to the tablet computer. In yet another alternative, the speaker may be mounted to glasses (e.g., Google Glass) that the operator of the apparatus 10 wears on his or her face. Many other alternatives will be apparent from this description.

The microphone may be a standalone microphone connected by wire or wirelessly to the tablet computer. As an alternative, the microphone 58 may be incorporated into the tablet computer 52 of which the video display screen is a component. A still further alternative is that the microphone may be a microphone incorporated into a smart phone that is operated by the operator of the apparatus 10. In yet another alternative, the microphone may be a wired or wireless microphone connected to the tablet computer. In yet another alternative, the microphone may be mounted to glasses (e.g., Google Glass) that the operator of the apparatus 10 wears on his or her face. Many other alternatives will be apparent from this description.

Figure 15:
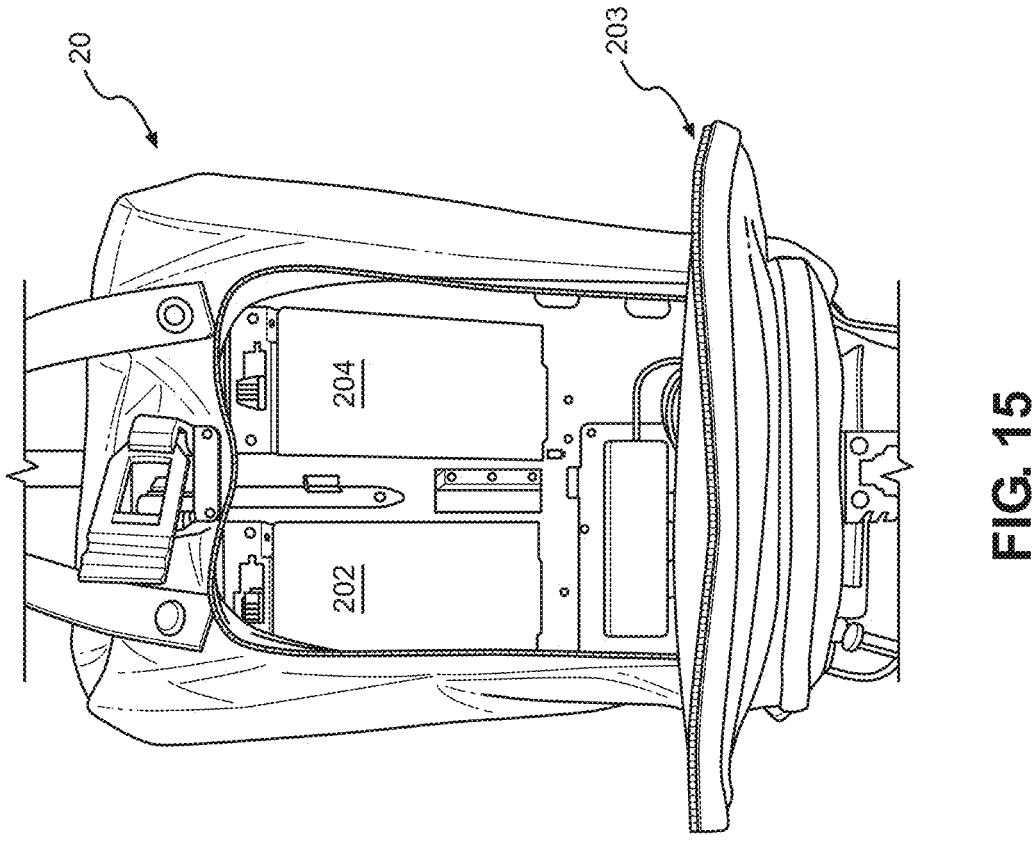
FIG. 15 is a rear view illustrating the embodiment of FIG. 14 with an access panel in an open position.
Figure 14:
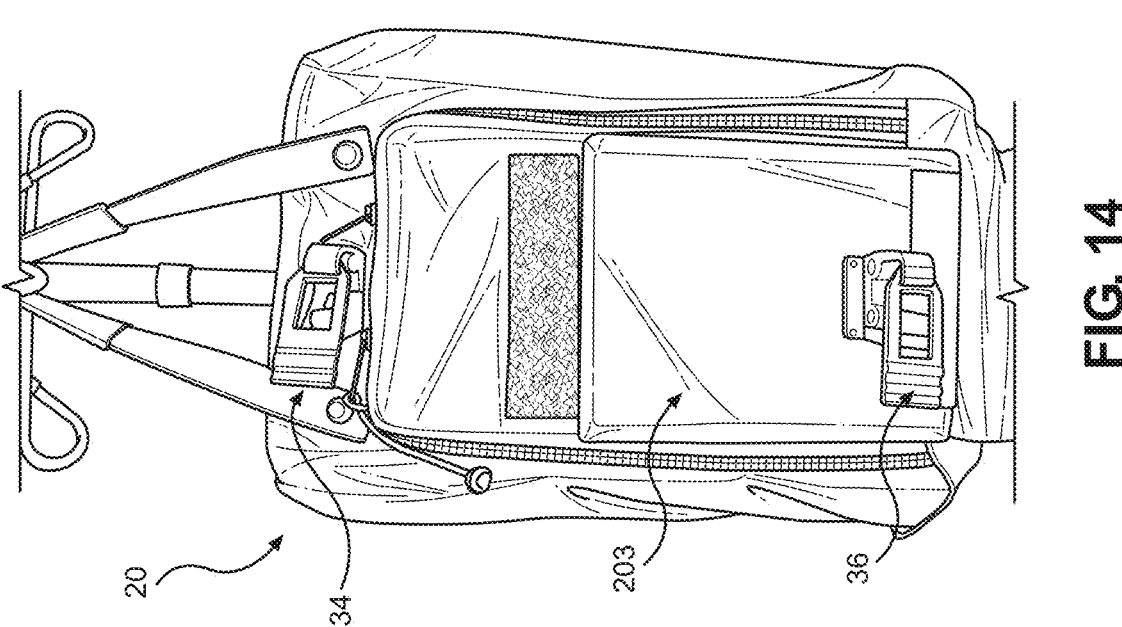
FIG. 14 is a rear view illustrating an embodiment of the present invention with an access panel in a closed position.

It is contemplated that the batteries 202 and 204, which are removably mounted to the computer 50 in a conventional manner, comprise the only power source in the case 20. It is contemplated that all of the electronic medical devices and the tablet computer 52 obtain electrical power from the single power source of the removably mounted batteries 202 and 204. The batteries 202 and 204 may be accessed through a battery access panel 203 that is fastened to the case 20 by removable fasteners, such as a zipper, hooks and loops fasteners or any other suitable fastener. The battery access panel 203 is shown in the operable position in FIG. 14, and in the open position in FIG. 15 where the batteries 202 and 204 are accessible for removal and replacement. The battery access panel 203 gives easy access to the battery compartment when the case 20 is in the open or closed configurations. This permits battery replacement while the apparatus 10 is operational.

Figure 4:
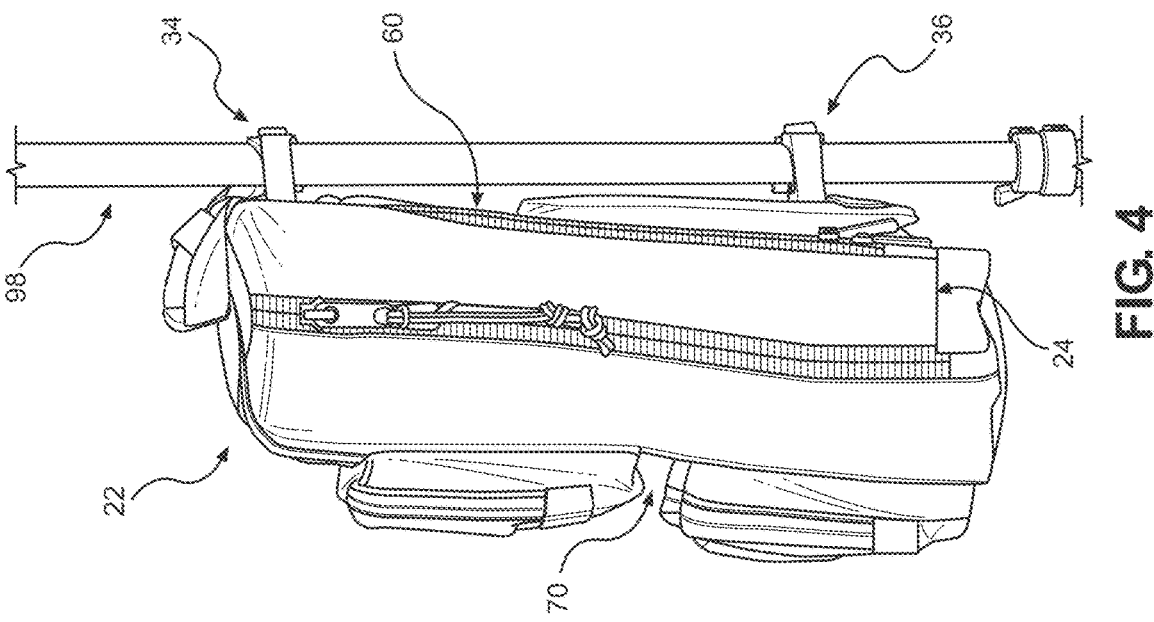
FIG. 4 is a side view illustrating the embodiment of FIG. 3.
Figures 5, 6:
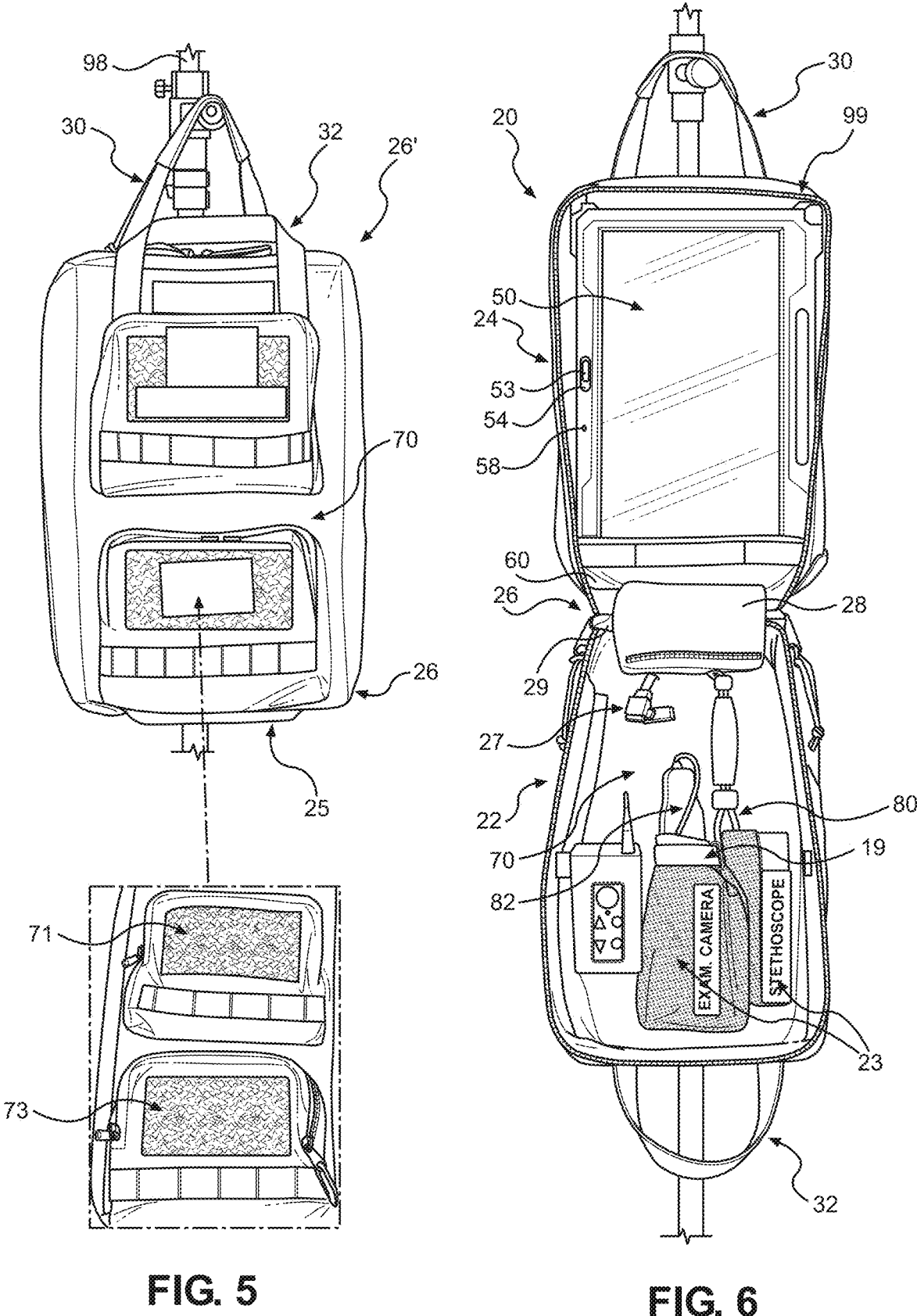
FIG. 5 is a front view illustrating an embodiment of the invention in a closed configuration and attached to a pole.
FIG. 6 is a front view illustrating an embodiment of the invention in an open configuration and attached to a pole.

As shown in FIGS. 3-6, the case 20 has a first portion 22 and a second portion 24. The first and second portions are components of the case 20 that pivotably attached to one another at one case end, which is the bottom end 26 when the case 20 is in an operable orientation, one of which is shown in FIG. 5. The first portion 22 is what would be considered at the "front" of the case 20 (in the closed configuration, explained below) because the first portion 22 faces the operator of the apparatus 10 when the case is in an operable orientation, such as the orientation shown in FIG. 5 with the case 20 hanging on the pole 98. The second portion 24 is preferably positioned at the rear of the case when in this operable orientation, with the pole 98 on the opposite side of the case from the user of the apparatus. Thus, the user ordinarily faces the apparatus 10 when the apparatus 10 is in the orientation shown in FIG. 5, and the first portion 22 is preferably closest to the user and farthest from the pole 98. Although the first portion 22 and the second portion 24 are described in locations defined relative to the user, it will be understood that the first and second portions may be relatively located differently with respect to the viewer or operator of the apparatus 10. For example, the apparatus 10 may be positioned with the first portion 22 in the rear closer to the pole 98 and the second portion 24 in the front relative to a viewer or operator.

In a preferred embodiment, the case 20 is made of a flexible fabric material similar to that of a backpack made for carrying a laptop or tablet computer, optionally with padding to protect the contents of the case and/or sheet inserts to make the structure more rigid. The case 20 may be made of flexible fabric, including without limitation canvas, nylon, rip-stop nylon, ballistic nylon, leather, denim, poly-vinyl chloride (PVC), and polyester. The case 20 may also include one or more flexible films, rigid plastics and/or any other suitable material inserted between layers of fabric or film to rigidify the fabric or film.

It is preferred that the case 20 be manufactured according to military specifications (MILSPEC), and that the case 20 be washable so that any contamination can be readily removed before the next use. Still further, it is preferred that the case 20 be lightweight, such as weighing a few ounces to one pound, so that it does not add significantly to the weight of the components carried therein. The first portion 22 may have, as shown in FIG. 5, front storage pouches 71 and 73, which preferably have hooks and loops fasteners and molle straps sewn onto the fronts thereof. The pouches 71 and 73 may hold power packs/batteries, electrical cords, and any other items. These function well for attachment of identification, medical or other patches and any gear that needs to be attached to the case 20.

As shown in the illustrations of FIGS. 2 and 6-8, the first portion 22 and the second portion 24 of the case 20 have a pivotable connection at the end 26. This pivotable connection may be a live hinge, such as the flexible panel 25 (FIG. 2) that is contiguous to both portions 22 and 24. In one example, the flexible panel 25 may be a part of the same piece of fabric of which the first portion 22 and the second portion 24 are made. The flexible panel may alternatively be non-removably attached to both the first and second portions 22 and 24, such as by being adhered or stitched, as shown in FIG. 2. Alternatively, the flexible panel may be separable from one or both portions 22 and 24 by a zipper or other fastener. Still further, the pivotable connection may be a conventional hinge. In the embodiment shown in FIG. 2, the flexible panel 25 is padded with a soft cushion sewn or otherwise attached thereto in order to protect the electronic components contained in the case 20 from damage if the case is dropped.

Each of the portions 22 and 24 may be generally rectangular and may include a substantially planar panel 60 and 70, respectively, that forms a major part of each of the portions. The first portion 22 may be removably aligned with the second portion 24 (see FIG. 5) by any suitable fastener along three or more common sides of the rectangular panels. Where the flexible panel 25 is attached at one side of the first portion 22, and is attached at one side of the second portion 24, the flexible panel 25 functions as a flexible "live" hinge about which the portions 22 and 24 pivot relative to one another. The remaining three sides of each portion may fasten to one another, such as by a zipper or any suitable fastener, as described below. In other embodiments, all four sides of the first and second portions may fasten to one another using a zipper and thus the first portion 22 is attached to the second portion 24 along four common sides. In the embodiment shown, a zipper 29 attaches the portions 22 and 24 along all three sides and along portions of the fourth side where the flexible panel 25 forms a live hinge connecting both portions 22 and 24 together. Of course, fasteners other than a zipper may be used, such as snaps, buttons, magnets, or any suitable fastener.

Side walls 62, 66, 72 and 76 and end walls 64 and 74 extend at a right angle to the respective planar panels 60 and 70 to which they attach and to the adjacent side walls or end walls to which they attach. Because each of the side walls and end walls is flexible, and because the planar panels 60 and 70 are flexible, the angles between the side walls and the planar panels to which they attach, and between the end walls and the planar panels to which they attach, may not be exactly 90 degrees, but will usually be within 5-20 degrees of 90 degrees.

Figure 3:
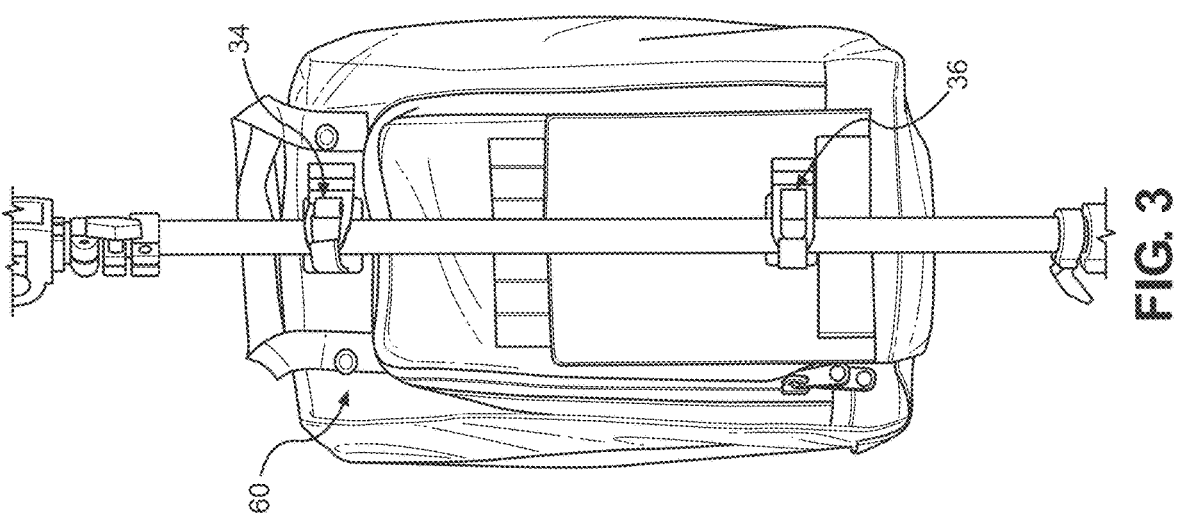
FIG. 3 is a rear view illustrating an embodiment of the invention mounted on a pole.

The apparatus 10 shown in FIGS. 3-5 is shown in a "closed" configuration in which the first and second portions 22 and 24 are fastened together by the zipper 29. The apparatus 10 is shown in an "opened" configuration in FIGS. 6-8. In the opened configuration, the first portion 22 is preferably positioned below the second portion 24 and is only connected to the second portion 24 by the pivotable connection, such as the flexible panel 25. The opened configuration permits viewing of the video display screen 50, as well as access to any instruments mounted in the first portion 22. In the opened configuration, the contents of the case 20, and the video display screen 50 in particular, are exposed to use and are more exposed to damage.

Each of the first and second portions 22 and 24 may form about one-half of the thickness of the case 20, although it is contemplated that each portion may form much more or much less than one-half of the case thickness. The thickness is in the direction along a line extending perpendicularly from the planar panel 70 of the first portion 22 to the planar panel 60 of the second portion 24. Fastener components, such as the complementary zipper teeth 68 and 78, may be attached to the distal edges of the side walls and end walls of each of the first and second portions by adhesion, welding or stitching. A complementary slider body 29 permits the portions 22 and 24 to be fastened to one another in the closed configuration. The portions 22 and 24, even in the closed configuration, remain removably attached so the first and second portions may be readily placed in the opened configuration in which the fasteners are not attached on some or all of the side walls and end walls.

It is preferred that, when in the closed configuration, the case 20 defines at least one chamber 99 therein, in which some or all communication components, which are described herein, may be contained. The chamber 99 is formed between the planar panels 60 and 70, as well as between the side and end walls 62, 64, 66, 72, 74, and 76, and the flexible panel 25. In the embodiment of FIGS. 5 and 6, the chamber 99 is the void formed within the case 20 where the tablet computer 52 is disposed when in the closed configuration. When the case is in the closed configuration, the chamber 99 is not visible or accessible by the operator from the exterior of the case 20 until the opened configuration is achieved. However, when the case 20 is in the opened configuration, the chamber 99 is exposed as shown in FIG. 6.

The chamber 99 may be accessed by removing the attachment of the fastener attaching at least three of the side and end walls of the first portion 22 to three corresponding side and end walls of the rear portion 24, such as by unzipping the slider body 29 around the first and second portions 22 and 24. In one embodiment, the chamber 99 contains the video display screen 50, which may be the screen of the tablet computer 52, along with other instruments. The instruments may be one or more of many kinds of medical examination instruments, such as may be commonly used to examine and/or treat human patients. As an example, the instruments may include a stethoscope 80 and a camera 82 that connect to the tablet computer wirelessly or using wires so that any signals produced thereby are conveyed to the tablet computer 52.

The first portion 22 may include one or more pockets 23 or other structures to retain in the chamber 99 the instruments that may be used during an examination or procedure on a patient. It is preferred that the pockets 23 are made of a mesh material with tightening straps 19 to safely seal devices inside the pockets 23. Mesh provides a view inside each pocket 23 of the equipment or device therein, along with access to air in case fluids are on the device. Two pockets 23 are preferred for the stethoscope, with an upper pocket for storing the stethoscope audio cable and a lower pocket for storing the stethoscope and a power cable for recharging. A communication device storage pocket 23 is also preferred. This pocket 23 is preferably removable from the case 20 for rapid customization using hooks and loops, or another fastener. Straps preferably lock in the communication device in the pocket. A hooks and loops strap is sewn in the pocket to lock devices in place for storage. The pockets 23 can also be renamed quickly with name strips removably fastened with hooks and loops fasteners.

The electronic/digital stethoscope 80 may be connected to the tablet computer 52 by wires, wirelessly or otherwise. The data produced by the stethoscope when a user places it on the patient is received by the tablet computer 52 and may be transmitted to a second party (e.g., a specialist) at a remote location, such as in a hospital many miles away, thereby permitting the second party to diagnose the patient's condition. Alternatively, an examination camera 82 may be connected to the tablet computer 52 by a wire or wirelessly. The user may direct the camera's lens, depending upon the type of camera, toward a desired location (e.g., a wound site), which may be on the exterior of the patient or may be internal to the patient. The data from this camera 82 is received by the tablet computer 52 and transmitted to the second party at the remote location. Other instruments may be desirably inserted in the pockets 23, and may be removed from the pockets and used after creating a wired or wireless data connection to the tablet computer 52.

An Ethernet port 27 (FIG. 6) or other suitable communications port may be connected to the tablet computer 52 and may extend from the tablet computer 52 under the panel 28 into the chamber 99. This permits ready accessibility to connect the port 27 by Ethernet cable to a computer network, whether in a hospital or a transport vehicle, such as an ambulance or an aircraft. Such a connection permits rapid data transfer, whether of live communication data or of data stored in the tablet computer 52 or another data storage device, which data may have been stored as a result of an earlier examination of a patient. The Ethernet port 27 may be attached to a strap or another structure using fasteners, such as zip ties, to affix the port 27 for predictably consistent location.

Figure 22:
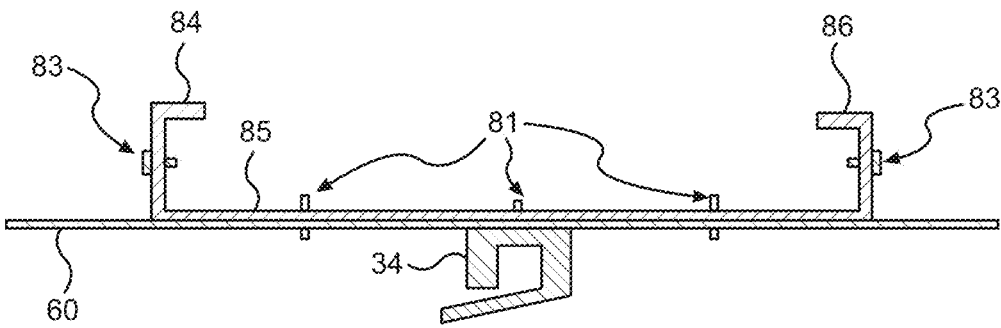
FIG. 22 is a schematic top view illustrating the attachment means shown in FIG. 21.
Figure 23:
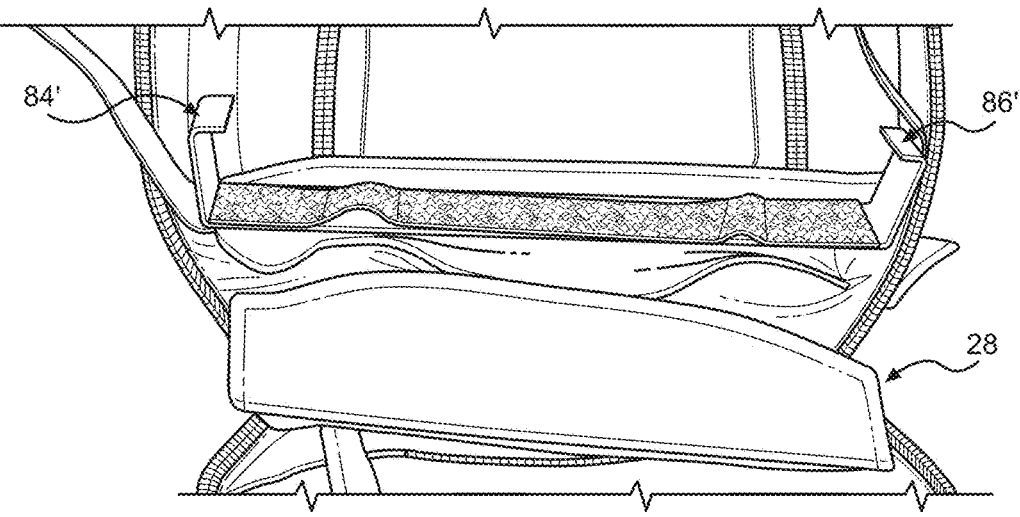
FIG. 23 is a front view illustrating a lower portion of an embodiment of the present invention with a tablet computer removed to show attachment means for a tablet computer.
Figure 24:
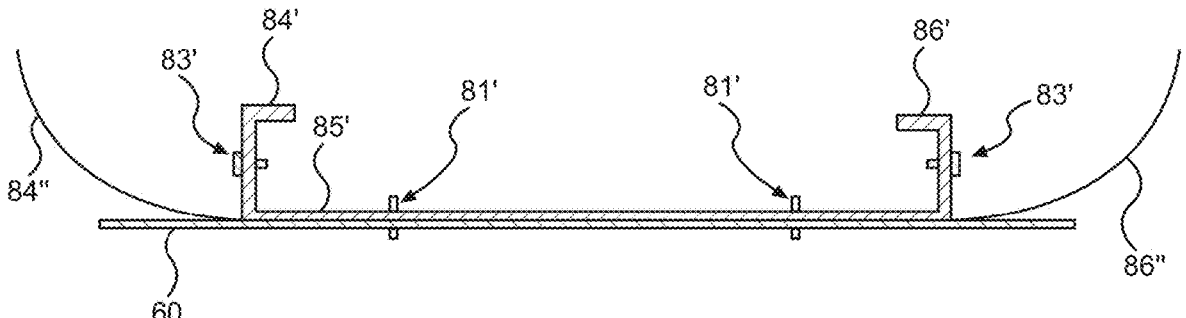
FIG. 24 is a schematic top view illustrating the attachment means shown in FIG. 23.

The video display screen 50 is mounted near an upper end to the second portion 24 as shown in FIGS. 6-7 and 21-22 such as by corner braces 84 and 86 that are terminal ends of a rigid bracket 85 that is mounted to the panel 60, such as by rivets 81 or any suitable alternative fastener. The braces 84 and 86 extend around, and rigidly retain, the upper corners of the tablet computer 52. Neural screws 83 may be used to tighten against and further secure the tablet computer 52 to the corner braces, as shown in FIGS. 22 and 27. These neural screws 83 are easily removed for disassembly and cleaning of the case 20. The upper clamp 34 is preferably mounted to the bracket 85, such as by rivets 81 or any suitable alternative fastener in order to provide sturdy support. In this manner, the clamp 34 is rigidly mounted to the bracket 85, with the panel 60 sandwiched therebetween, and this configuration creates a rigid connection between the tablet computer 52 and the pole 98 to which the apparatus is mounted. A rigid connection is one that would not visibly bend under forces the apparatus is expected to encounter during normal use.

The video display screen 50 is mounted near the lower end 26 to the second portion 24 as shown in FIGS. 6-7 and 23-24. This may be by corner braces 84' and 86' that are terminal ends of a bracket 85' that is mounted to the panel 60, such as by rivets 81' or any alternative suitable fastener. The hooks and loops fastener straps 84" and 86" that extend between the bracket 85' and the panel 60 may further supplement the attachment. The braces 84' and 86' extend around, and rigidly retain, the lower corners of the tablet computer 52, and are not visible in FIG. 7 because the straps 84" and 86" cover the braces 84' and 86', respectively. Nevertheless, the braces 84' and 86' are positioned in a similar position relative to the lower end of the tablet computer 52 as the braces 84 and 86 are to the upper end of the tablet computer 52. Neural screws 83' may be used to tighten against and further secure the tablet computer 52 to the corner braces.

The lower clamp 36 may be mounted to the bracket 85', such as by rivets or any suitable fastener, with the panel 60 and the straps 84" and 86" sandwiched therebetween, in order to provide a sturdy support. Thus, the clamp 36 may be rigidly mounted to the bracket 85', which creates a rigid connection between the tablet computer 52 and the pole to which the apparatus is mounted.

As shown in FIGS. 16-18 and 23-24, the panel 28 has an upper end with a fastener, which may be the hooks and loops strip 88. The upper end of the panel 28 may be placed over the front of the lower end of the tablet computer 52, with the strip 88 aligned parallel with the bracket 85' on the rear of the tablet computer 52. The strip 88 and the panel 28 are shown in an operable position in FIG. 16. Complementary hooks and loops fastener straps 84" and 86" extend from behind the bracket 85' and over the respective braces 84' and 86' and attach to the strip 88. This fastens the panel 28 to the lower end of the tablet computer 52 and the bracket 85'. The remainder of the panel 28 extends toward the portion 22 across and overlapping the flexible panel 25 to attach to the portion 24. The panel 28 is shown in an operable position in FIG. 16. The portion of the panel 28 that overlaps the flexible panel 25 forms a passage between that portion and the flexible panel 25 through which wires 330 and 332 may extend from the tablet computer 52 to the instruments in the portion 22.

Any other suitable fasteners for holding the video display screen, tablet computer or other visual display may be substituted for the fasteners shown and described. For example, a pocket with a transparent film may retain the video display screen. Alternatively, a fastener such as hooks and loops material may removably attach the rear of the tablet computer 52 to a complementary material mounted to the panel 60 of the second portion 24. These do not have the benefit of direction connection between the pole 98 and the bracket 85 that rigidly retains the tablet computer. Nevertheless, they are contemplated.

Figures 16, 17, 18:
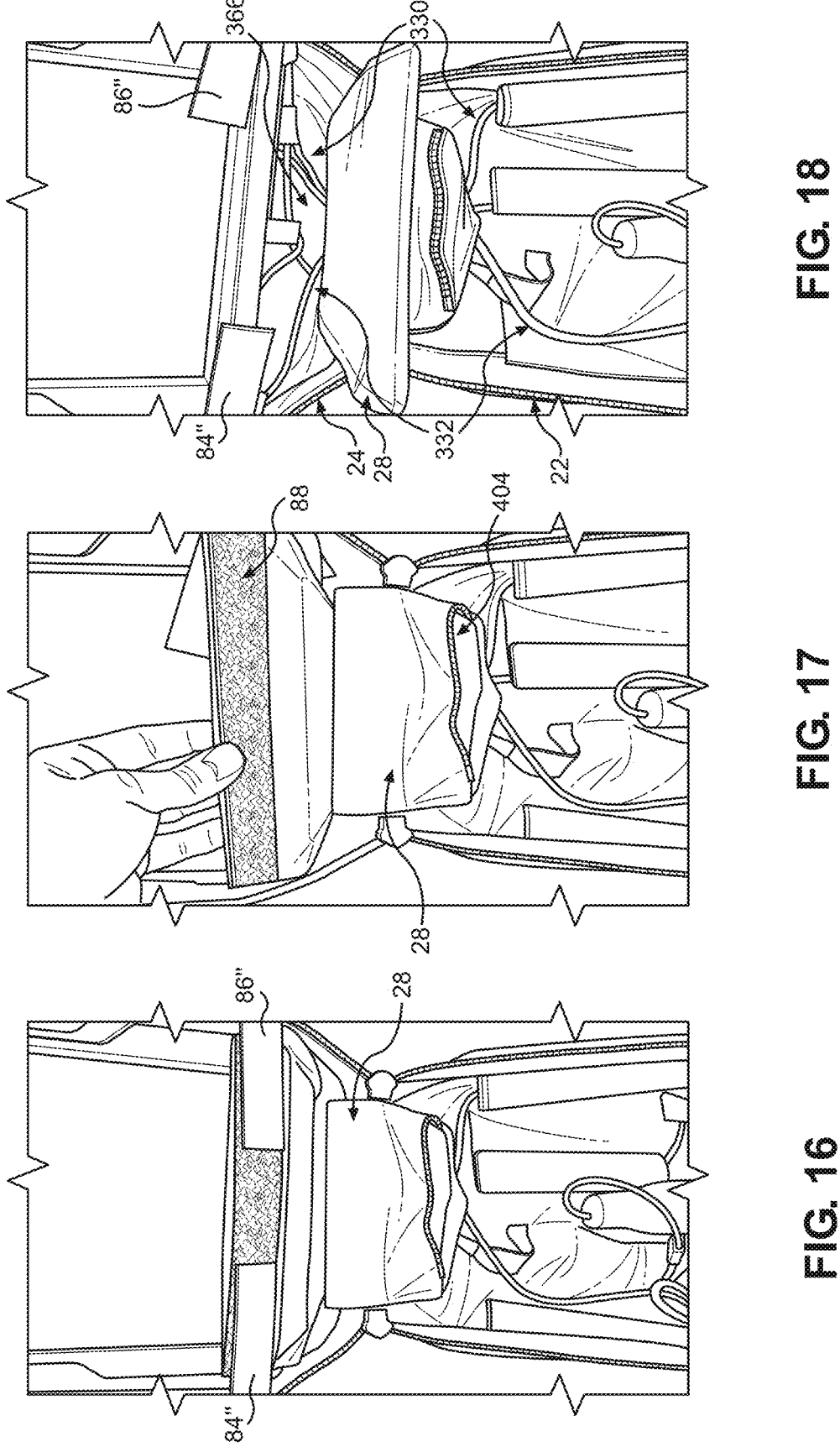
FIG. 16 is a front view illustrating an embodiment of the present invention in an opened configuration.
FIG. 17 is a front view illustrating the embodiment of FIG. 16 with the panel 28 in a state of removal.
FIG. 18 is a front view illustrating the embodiment of FIG. 16 with the panel 28 in a further state of removal.

A chamber 366 may be formed in the portion 24, between the rear of the tablet computer 52 and the panel 60, as shown in FIG. 18. This chamber 366 may be accessed by opening the battery access panel 203 (described below) or removing the panel 28 or a part of the panel 28. This is accomplished as shown in FIGS. 16-18 by removing the straps 84" and 86" from the strip 88 and then manually pulling the panel 28 away from the tablet computer 52. This exposes the chamber 366, with wires 330 and 332 extending from the chamber

Figure 19:
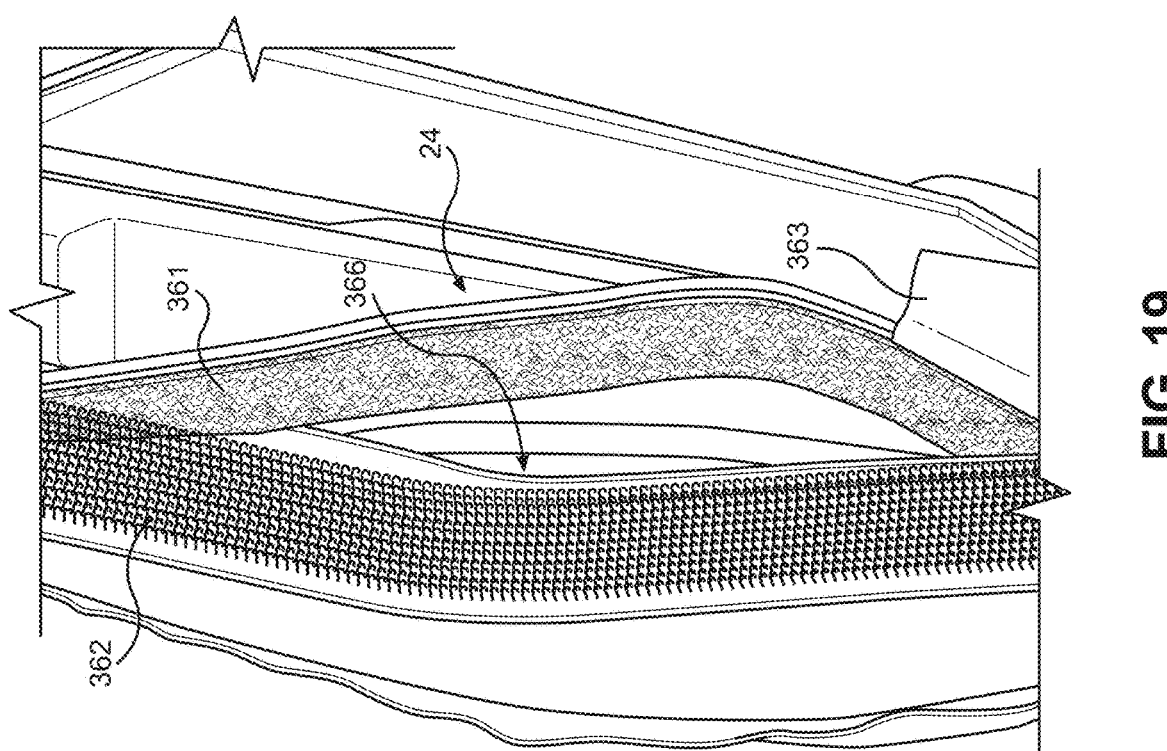
FIG. 19 is a side view illustrating an embodiment of the present invention with an access opening to a chamber opened.
Figure 21:
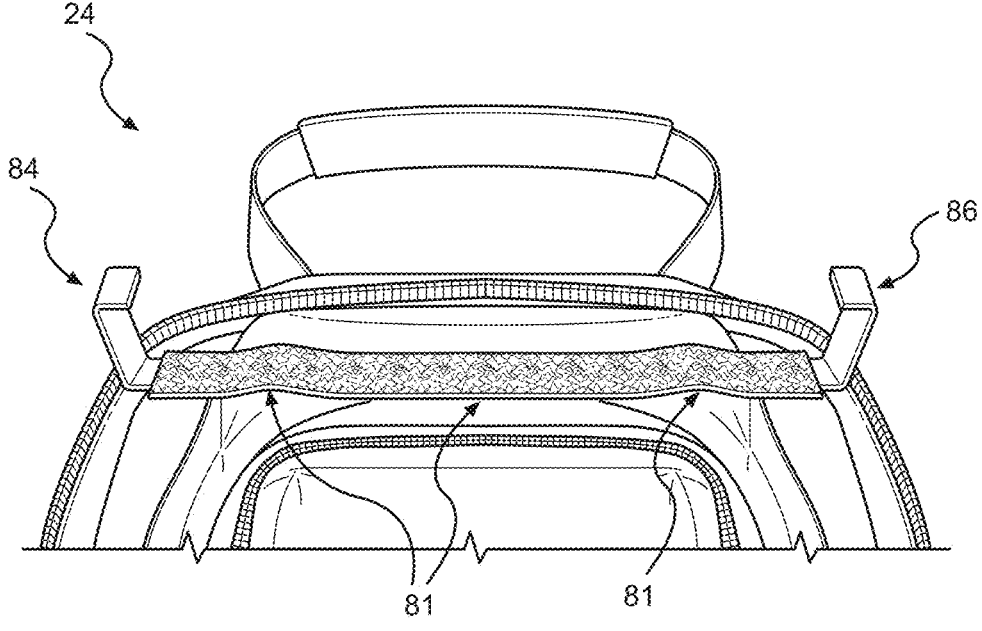
FIG. 21 is a front view illustrating a top portion of an embodiment of the present invention with a tablet computer removed to show attachment means for a tablet computer.

366 to where the instruments are stored. The chamber 366 may also be accessed through the fasteners, which may be complementary hooks and loops material, formed on the edges 361 and 362 shown in FIG. 19. The chamber 366 may be accessed in this manner by grasping the tab 363 and separating the edges 361 and 362.

Figure 8:
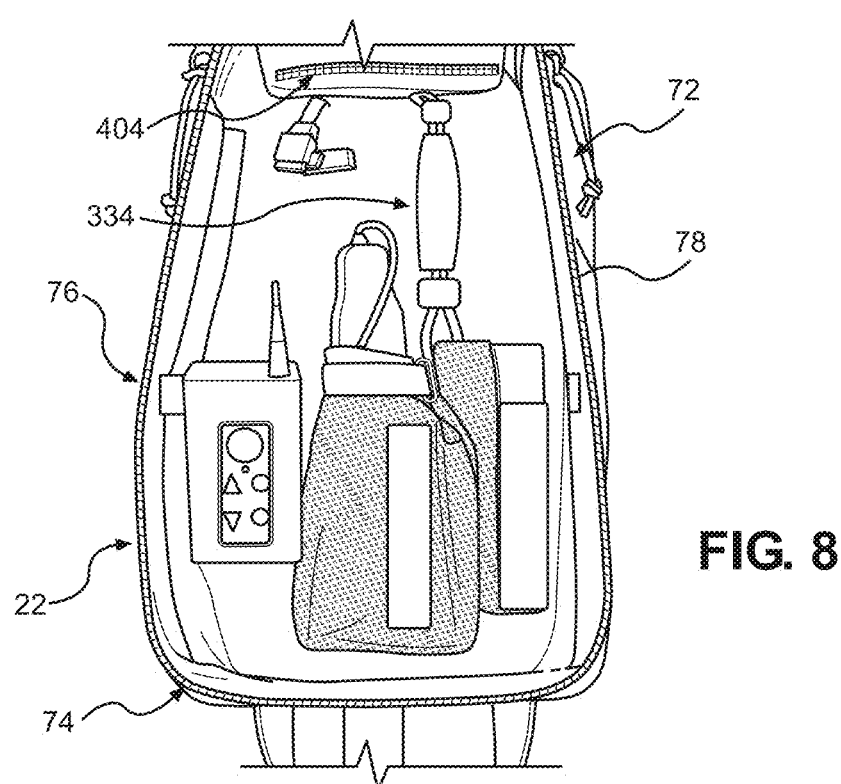
FIG. 8 is a front magnified view illustrating the lower portion of the embodiment of FIG. 6.
Figure 9:
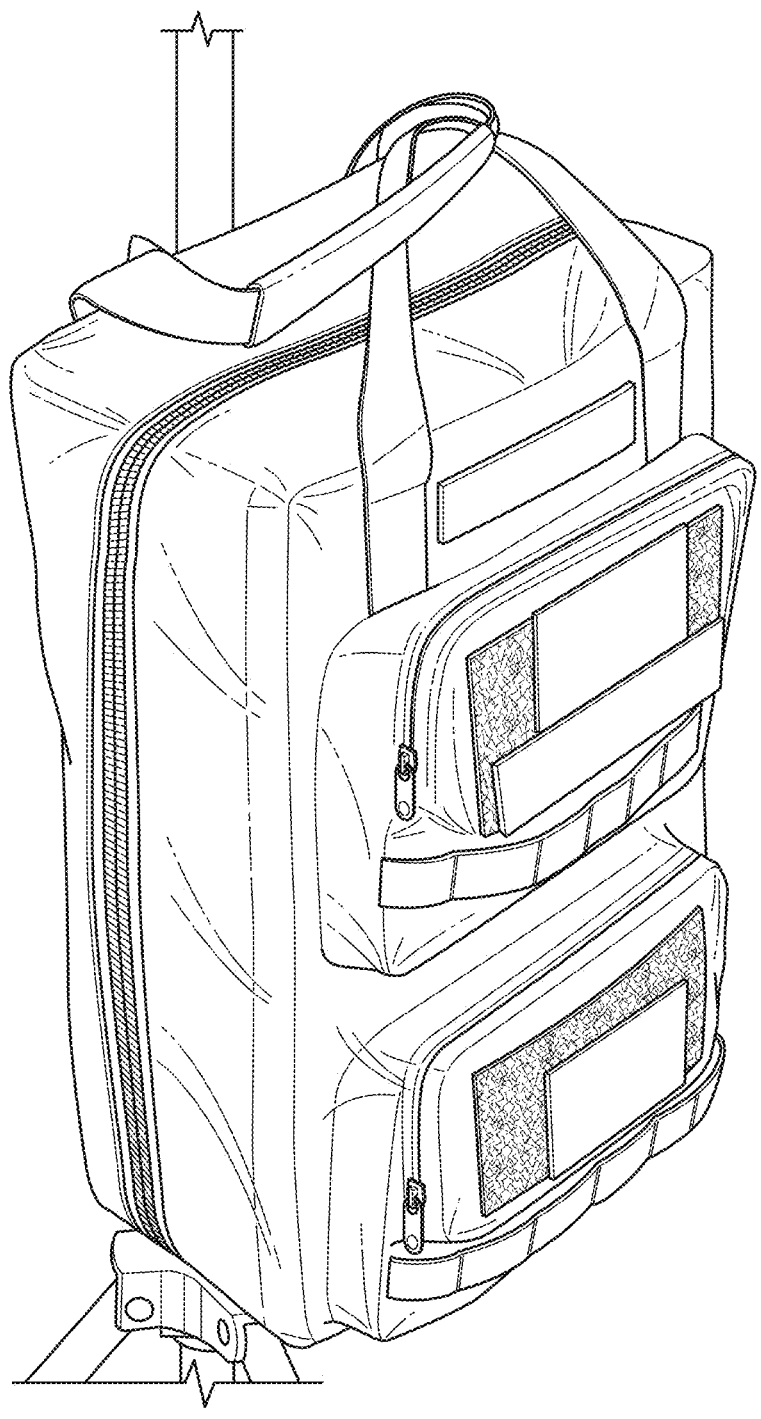
FIG. 9 is a view in perspective illustrating the embodiment of FIG. 3.
Figure 20:
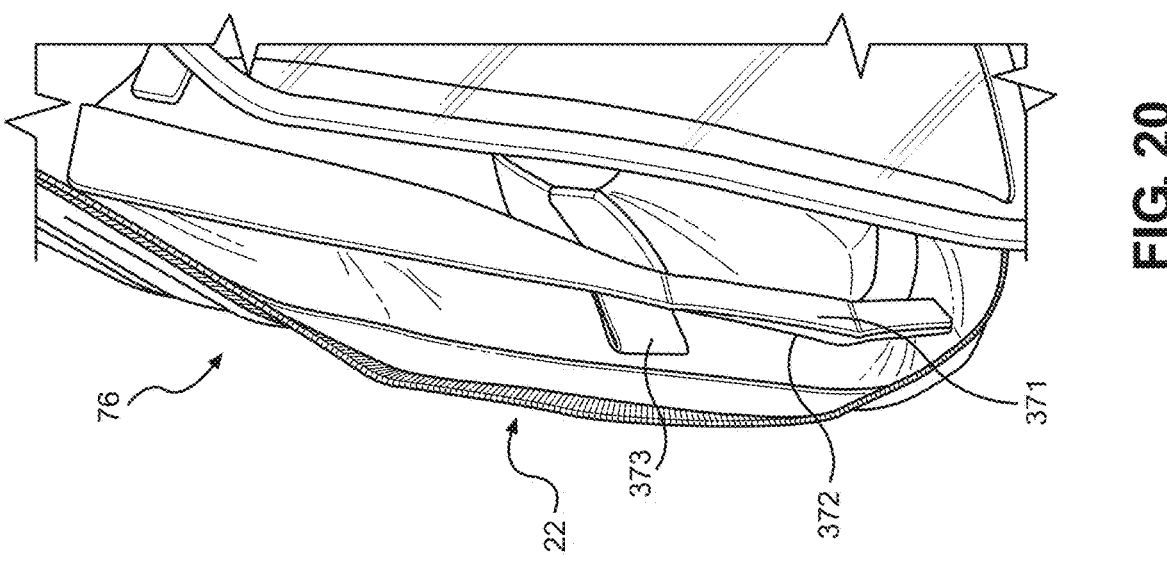
FIG. 20 is a side view illustrating an embodiment of the present invention with an access opening to a chamber exposed.

Wires in a bundle 334 may extend from the chamber 366 beneath the panel 28 and then to the instruments, as shown in FIG. 8. Another passage for wires may be found in the portion 22, as shown in FIG. 20, where two edges 371 and 372 are attached. The edges 371 and 372 may be attached using hooks and loops fasteners, similarly to the edges 361 and 362 described above. The tab 373 may be grasped to separate the edges 371 and 372 and expose the passage that is similar to, but preferably smaller than, the chamber 366. Wire management is an important feature of the case, because when medical treatment is needed, tangled wires could result in harm to the patient.

Figure 7:
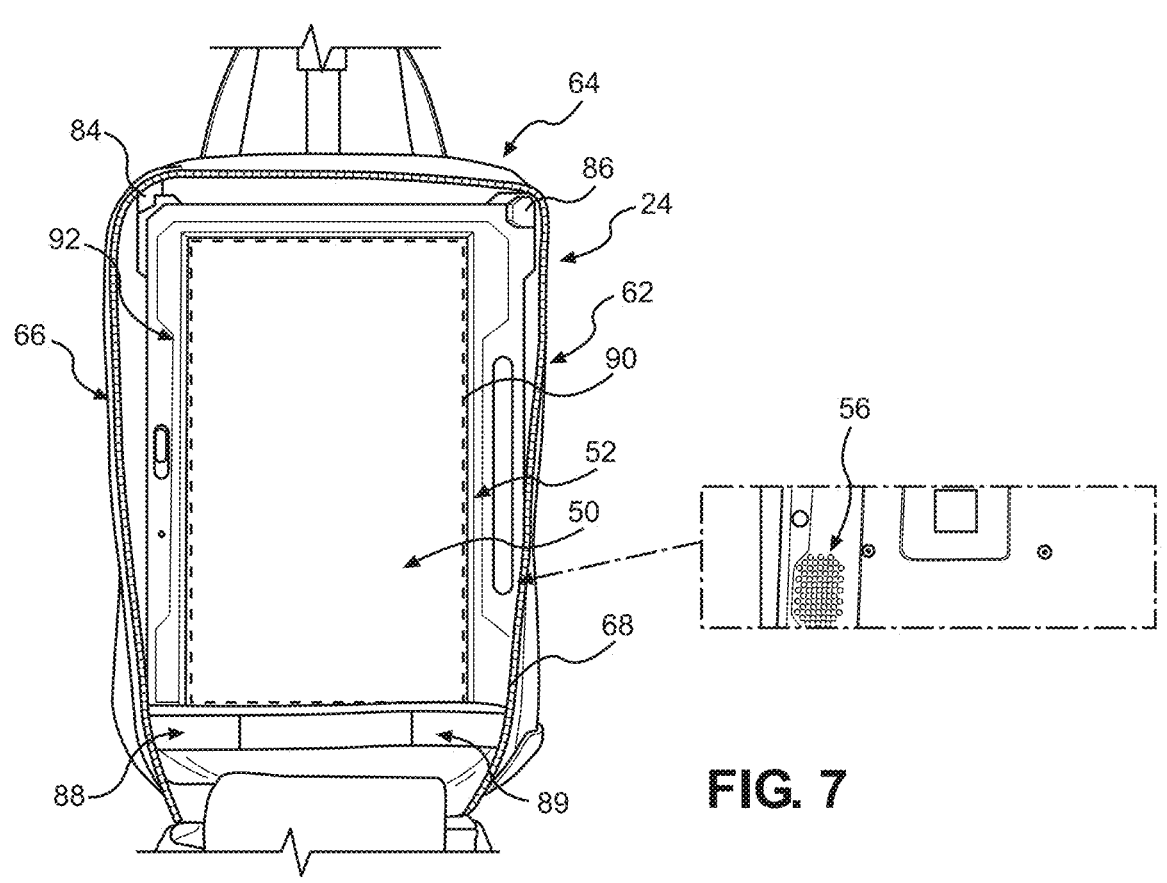
FIG. 7 is a front magnified view illustrating the top portion of the embodiment of FIG. 6 and a view of a portion of the rear of a portion of the tablet computer.

The video display screen 50 has a viewable region 90 that is within the dashed box shown in FIG. 7 designated by reference numeral 90. This viewable region 90 faces away from the planar panel 60 of the second portion 24 when the video display screen 50 is mounted to the second portion 24 as shown in FIGS. 6-7. The viewable region 90 is the portion that displays images according to the data received by the tablet computer 52, and is commonly what is called the "display surface" of a video screen. In the embodiment shown, the viewable region 90 excludes the opaque border structure 92 that surrounds the display surface on four sides, and it excludes the rear housing of the video display screen 50. The rear housing is not visible in FIGS. 6-7, but is well known in the industry and may be seen in FIG. 15. The viewable region 90 is the portion of the video display screen 50 that displays images the operator may view using his or her eyes during operation of the apparatus 10, and typically faces the operator during operation.

When the first and second portions 22 and 24 are in the closed configuration, shown in FIGS. 1-5 and 9, the first and second portions 22 and 24 form the enclosed chamber 99 in which the video display screen 50 is positioned with the viewable region 90 facing toward, and obstructed by, at least the first portion 22, such as the first portion's planar panel 70. Although the video display screen 50 is not visible in FIGS. 1-5 and 9, which show the closed configuration, the video display screen 50 is visible in FIGS. 6-7, which show the opened configuration. When the first portion 22 is pivoted upwardly about the flexible panel from the opened position shown in FIG. 6 to the closed position shown in FIG. 5, the video display screen 50 is not moved from the position that is shown in FIGS. 6-7. A preferred fastener, such as the zipper, may be fastened all around the adjacent side walls and end walls of the first and second portions 22 and 24 in order to fasten the first and second portions 22 and 24 to one another. In this closed configuration, the viewable portion 90 of the video display screen 50 is completely obstructed by the first portion 22 as can be seen in FIG. 5. In order to view the display screen's 50 viewable region 90, the apparatus 10 must be modified to the opened configuration, which is shown in FIG. 6. To do so, the zipper or other fastener is simply un-fastened in a conventional manner, and the first portion 22 is pivoted from the position shown in FIG. 5 to the position shown in FIG. 6.

One advantage of the apparatus 10 is that it may be readily operated when in the opened configuration, and the opened configuration is possible during transit of the patient on the human transport. The opened configuration is attained by the first portion 22 pivoting downward to beneath the second portion 24 and video display screen 50. In this position beneath the second portion 24 and the video display screen 50, the first portion 22 ceases to obstruct (and protect) the video display screen 50. This permits a viewer to observe images displayed on the viewable portion 90 of the video display screen 50, while also having access to the contents of the first portion 22 that is exposed by the position of the first portion 22 when in the opened configuration. However, in order for the apparatus to be used during transit of the patient, it is preferable to attach the apparatus 10 to a stable structure.

Figure 10:
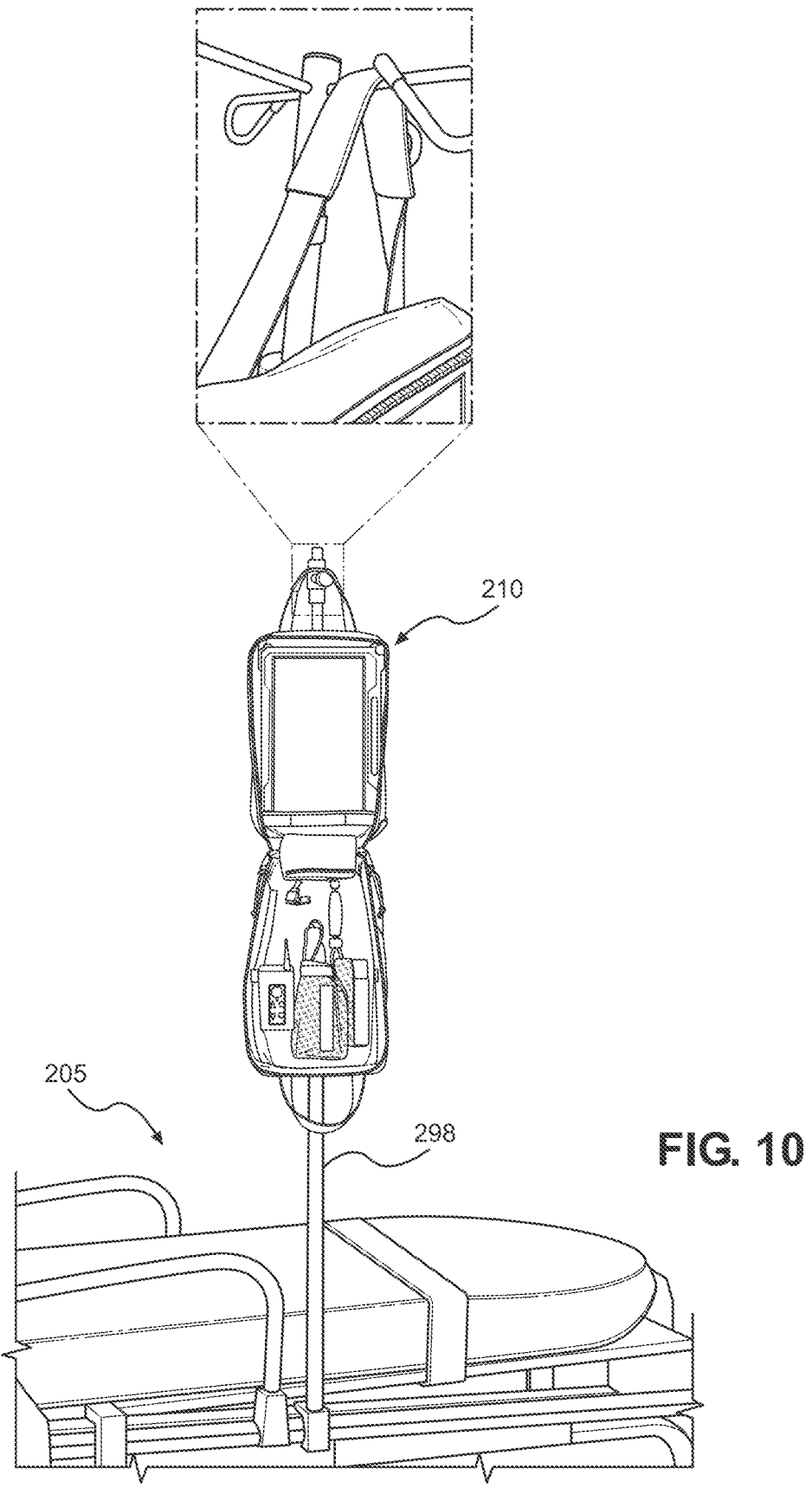
FIG. 10 is view in perspective illustrating an alternative embodiment of the present invention with a portion magnified.

A hanger, such as the second portion flexible loop 30 is mounted to the second portion 24 near a second case end 26' that is opposite the first case end 26. In some embodiments, the hanger includes an optional first portion flexible loop 32 that is attached to the first portion 22 at or near the second end 26'. In some embodiments, the loops 30 and 32 have a rubber, or other high-friction material, coating over at least a portion to reduce the probability of slipping. The hanger, in whatever form, is configured for hanging the case 20 in at least the opened configuration as show in FIG. 6. In a preferred embodiment, the hanger is also configured to hang the case 20 in the closed configuration. The loop 30 is mounted, such as by stitching or adhesive, to the second portion 24. The loop 32 is mounted, such as by stitching or adhesive, to the first portion 22. One or both of the loops 30 and 32 may be extended over a hook or other structure that permits the hanging of the apparatus 10. As shown in FIGS. 5, 6 and 10, the loop may extend over a knob or other structure that protrudes from the pole 98. In some embodiments, the pole 98 is a so-called "IV [intravenous] pole," which is a conventional device that may hold an IV bag filled with fluid that is commonly connected by tubes to a patient to cause the fluid in the bag to flow by gravity into the patient's blood vessels. When the pole 98 is an IV pole, the loop 30 and/or loop 32 may extend over the hook(s) designed to hold IV bags. These hooks are well-suited to accept the hooks 30 and 32 and securely retain the apparatus 10. As shown in FIG. 10, the loop 30 may be a hanging strap designed with a rubber grip material on the exterior to prevent or mitigate slipping on IV poles.

The hanger may alternatively or additionally be formed by the clamps 34 and/or 36 that are mounted to the panel 60 of the second portion 24 as shown in FIGS. 3 and 4 on the opposite side from the video display screen 50. The clamps 34 and 36 may be conventional pole clamps (e.g., QUICK-FIST brand rubber clamp) that permit clamping of the case 20 to the conventional IV pole 98. The clamp 34 is preferably near the second case end 26' and the clamp 36 is preferably farther from the second case end 26' to prevent swinging of the case 20 during movement. The loop 30 may be used alone to hang the apparatus 10 on a hook. Alternatively, the clamp 34 may be used alone to hang the apparatus 10 on the pole. In another alternative, any combination of the loop 30, the loop 32, the clamp 34 and the clamp 36 may be used to hang the apparatus 10. In a preferred embodiment, at least the loop and both clamps 34 and 36 are used to hang the apparatus 10 to the pole 98. When the loop and both clamps 34 and 36 attach to the IV pole, the case 20 is extremely limited in its ability to swing about the loop 30. The loops 30 and 32 and the clamps 34 and 36 assist with safe mobility, by securing the case 20 to a structure that will retain it, while delivering care to a patient. Thus, even if a significant force is applied, the hanger will retain the apparatus and prevent it from coming free and possibly striking someone nearby.

When the first and second portions 22 and 24 are in the opened configuration, as shown in FIGS. 6-8, the first portion 22 is positioned beneath the second portion 24 and beneath the video display screen 50. In this position, the first portion 22 does not obstruct the viewable region 90 of the video display screen 50 as when the case 20 was in the closed configuration of FIG. 5. Instead, when in the opened configuration, no part of the first portion 22 obstructs the viewable region 90 of the video display screen 50. However, in the closed configuration, the first portion 22 obstructs at least part of, and preferably the entirety of, the viewable region 90 of the display screen 50. In the closed configuration, the viewable region 90 is obstructed and protected by the first portion 22, and in the opened configuration the viewable region is unobstructed and unprotected by the first portion 22.

Figure 11:
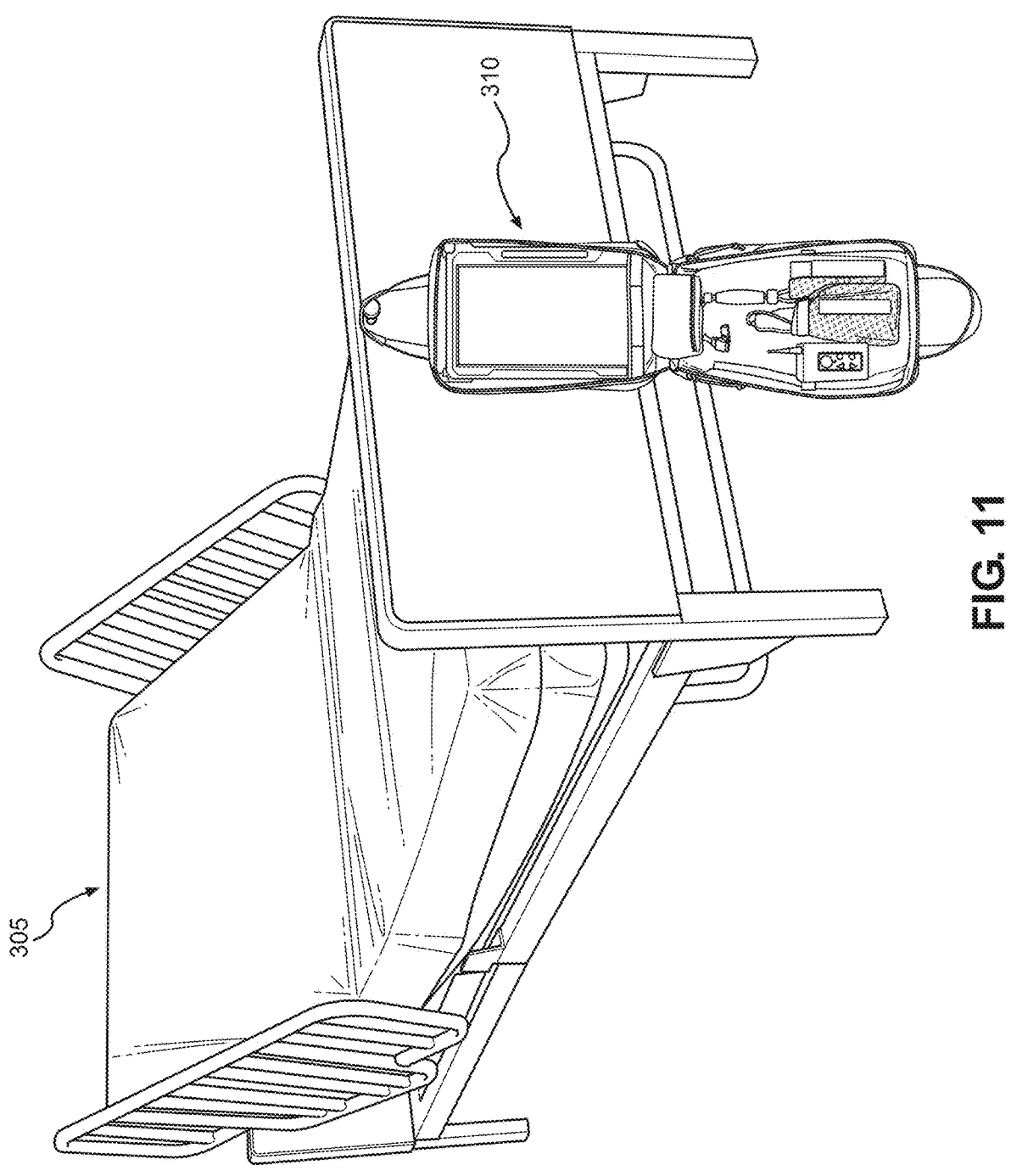
FIG. 11 is a view in perspective illustrating an alternative embodiment of the present invention.

The pole 98 may be attached to a human transport, which is any device designed to transport a human patient in a horizontal position. A human transport may be what is commonly referred to as a litter, a gurney, a hospital bed, a stretcher, or any other structure with a platform upon which a human patient may rest while the patient is transported from one location to another. As shown in FIG. 10, a gurney 205 may have an IV pole 298 mounted to the frame thereof and to which an embodiment of the apparatus 210 may be mounted by hanging a loop over an IV hook on the pole 298. Another alternative is shown in FIG. 11 in which a hospital bed 305, shown with wheels to permit transport of a patient, has an apparatus 310 in accordance with the present invention hanging from a hook at the footboard of the bed 305. Such a configuration may be advantageous in order to position the video display out of the view of the patient in the bed 305, for example in case the patient is a child. In the embodiments of FIGS. 10 and 11, the apparatuses 210 and 310, respectively, are mounted to the frame or other structures of the human transport.

An ambulance, helicopter, plane, or similar vehicle may also be considered a human transport, assuming a human patient may rest horizontally during movement. Ambulances have horizontal structures upon which patients may be placed for transport, and/or accommodate gurneys and litters with connection mechanisms. There are hooks and other structures within ambulances upon which the loop 30 may be hanged for disposing the apparatus 10 for use during movement of the ambulance. Because the apparatus 10 may be secured to any hook or other structure to which an IV bag may be secured, and because such hooks are prevalent in ambulances and other medical environments, the apparatus 10 is particularly well-suited for being secured in these environments.

As shown in FIG. 10, the case 20 is mounted to a pole that is mounted to the gurney. In this case, the gurney is the human transport upon which a human patient may rest while he or she is being transported by medical personnel. During the transport, the apparatus 10, which includes the case 20 and its components, may be operated, as noted above. Thus, the loop 30 hangs the case 20 on the pole, thereby permitting the apparatus 10 to be modified to the opened configuration while the human transport is in motion. The attending medical personnel may use the instruments located in the case 20 to collect data regarding the patient's medical condition that may be transmitted by the apparatus 10 to a distant second person, such as a medical specialist in a different hospital. The parties may communicate using audio and video alone by speaking and/or demonstrating using hand or arm gestures, and/or the second person may simply receive the data collected at the location of the patient. In one embodiment, the local (to the patient) medical person records data from the patient under verbal instruction by the medical specialist. In this situation, the apparatus 10 transmits the audio and video data, along with the recorded or live medical data, to the medical specialist who receives the same on a second apparatus, which may be similar or identical to the apparatus 10. The medical specialist verbally advises the local medical personnel to carry out particular medical procedures and observes the procedures by watching the video screen. Upon completion, updated data are sent to the medical specialist, who may be satisfied the procedure was carried out according to plan. All of this occurs while the apparatus 10 is in the opened configuration, and attached to a pole as described above, while the patient is in motion, such as resting in a litter that is mounted to a medical helicopter that is in transit to the hospital where the medical specialist is located.

As an alternative to attaching the apparatus 10 to a pole that is attached to the gurney, the case 20 may be attached to a hook on the headboard or the footboard, or it may be attached to the tubular side rail member, or any other conventional component of the gurney. In one example, the clamps 34 and 36 are the only hanger members that attach the case 20 to the pole 98 or side rail members of a litter. In another example, an IV pole's hook extends through the loop 30 and the case 20 hangs from the pole 98. In another example, the pole 298 may be attached to the frame of the gurney 205 or other structure the patient rests upon. In another example, a loop of an apparatus is mounted to a hook on the hospital bed footboard or other component of a hospital bed 305.

A stand 94 may be mounted to the case 20 to provide another alternative hanger. The stand 94 is shown in a collapsed position in FIG. 2, and may be disposed in a deployed position shown in FIG. 1. FIGS. 30-33 show illustrations during the process of deploying (and collapsing by reversing the process). When not in use, the stand 94 is collapsed substantially parallel to the panel 60 of the second portion 24, and does not protrude substantially from the second portion 24. The fastener components 494A, 495A, 496B, and 497B maintain the parts of the stand 94 substantially parallel to the panel 60 when the stand 94 is collapsed, as described below. When deployed as shown in FIG. 1, the stand 94 permits the case 20 to rest in a substantially vertical position, or within about thirty degrees from vertical, on a horizontal surface.

Figure 31:
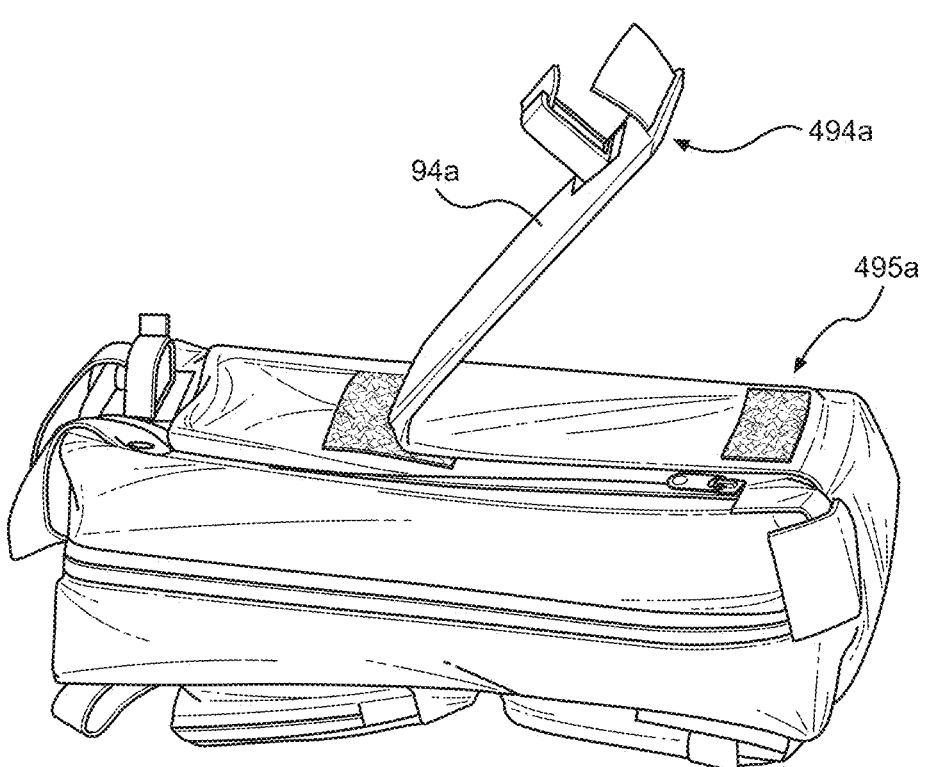
FIG. 31 is a view in perspective illustrating the embodiment of FIG. 30 with the stand in a process of deployment.
Figures 32, 33:
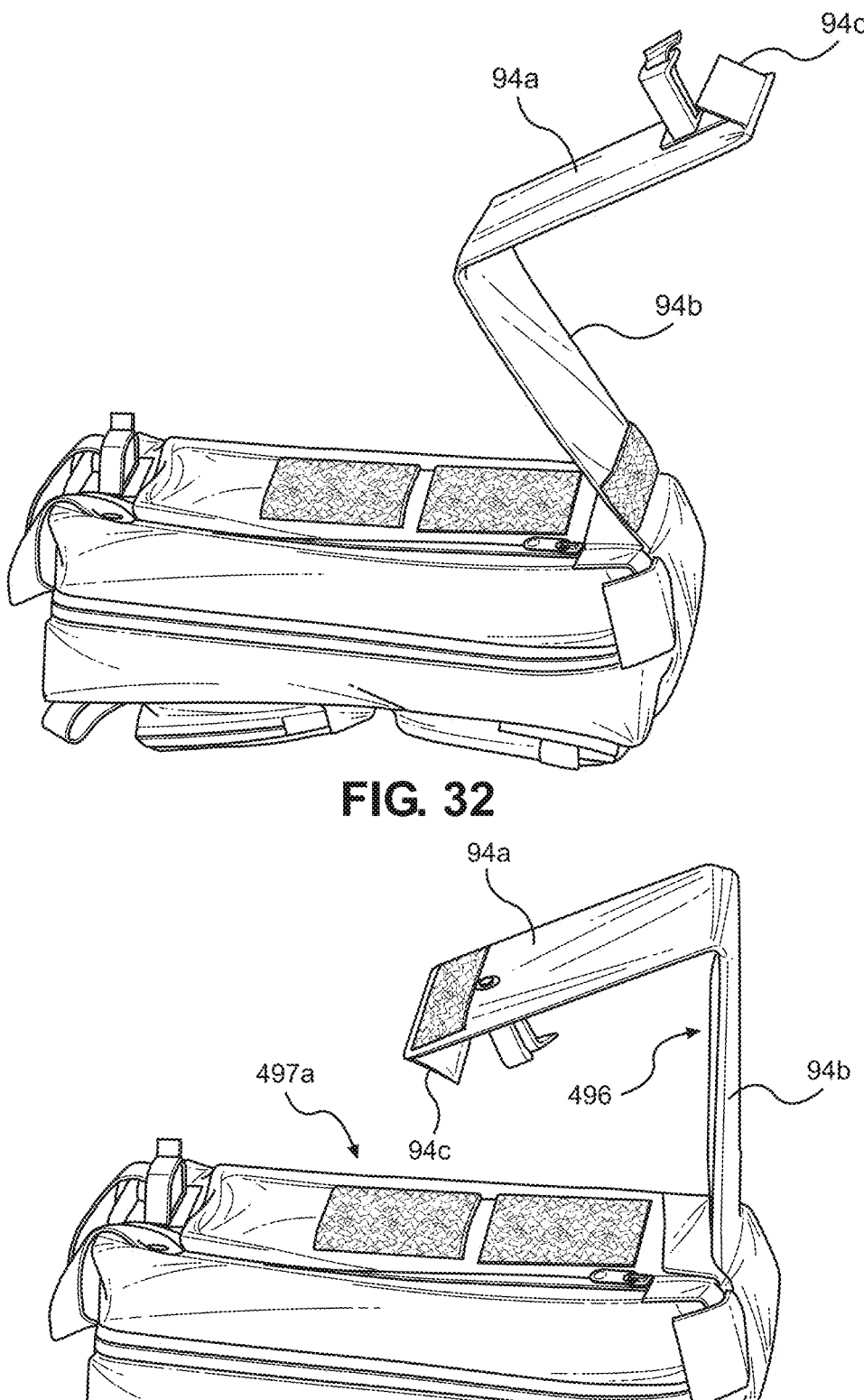
FIG. 32 is a view in perspective illustrating the embodiment of FIG. 30 with the stand in a process of further deployment than FIG. 31.
FIG. 33 is a view in perspective illustrating the embodiment of FIG. 30 with the stand in a process of further deployment than FIG. 32.

Deployment can be achieved by a process initiated by disposing the first leg 94A of the stand 94 transverse to the panel 60 as shown in FIG. 31. There may be a fastener, such as the complementary hooks and loops components 494A and 495A mounted to the first leg 94A and the second leg 94B, that must be detached before the first leg 94A is disposed in this position. The second leg 94B of the stand 94 is then disposed transverse to the panel 60 and transverse to the first leg 94B, as shown in FIG. 32. There may be a fastener, such as the complementary hooks and loops components 496B and 497B (FIG. 33) mounted to the second leg 94B and the panel 60, that must be detached before the second leg 94B may be disposed in this position. Finally, the third leg 94C is mounted to the component 497B with the third leg 94C parallel to the panel 60, such as by the complementary hooks and loops fastener that is mounted to the third leg 94C. The deployed configuration is shown in FIG. 1.

When in the deployed configuration shown in FIG. 1, the case 20 may be placed on a table, the floor or another horizontal surface with the second portion 24 in a generally vertical orientation (within 30 degrees of vertical) even when it is not possible or desirable to hang the case 20 from a hook, such as the loop 30. Being disposed in this position and held vertical by the stand 94 makes it difficult for the first portion 22 to be below the second portion 24 and the video display screen. However, if the case is disposed near an edge of the table, this is still possible because the first portion 22 may hang over the edge of the table.

In some embodiments, the panels 94A, 94B and 94C are made with canvas and are reinforced with rigid plastic panels for durability and strength to hold the case 20 in position when in the deployed configuration. The case 20 is designed to be used on the ground or any generally horizontal surface and angled upwards at about a 30 degree angle. Panel 94A is lifted upward and pulled away from the hooks and loops fasteners described above. The panel 94B is then pulled upward from the hooks and loops fasteners. The third step is to flip the first panel 94A over and attach the hooks and loops on the third panel 95C to the hooks and loops fastener sewn to the battery access panel 203 that is a part of the panel 60.

The apparatus 10 may be used to communicate between first and second parties in separate locations, such as a doctor in one location and a medic in an entirely different location. For example, the medic may be in the remote battlefield location and the doctor may be in a hospital many miles from the medic and patient. This is a common scenario during military operations. The patient may be disposed on a human transport, such as a litter, after being wounded. Once the patient is disposed on the litter, the communication apparatus 10 may be mounted to the litter, as has been described above or in any other manner. Then the apparatus 10 may be placed in the opened configuration and used by a medic and a medical specialist while the patient is being transported to the hospital.

As noted above, the communication apparatus 10 includes at least a wireless transceiver that is able to transmit and receive wireless signals, and this may be a cellular telephone. The apparatus 10 also includes a camera, a speaker, a microphone, and a video display screen that is mounted to the case. The preceding components may be integral components on the tablet computer 52 that is mounted to the second portion 24 of the case 20. The first portion 22 is pivotably mounted to the case 20 at the first case end, which may be the bottom when disposed in an operable orientation. The video display screen mounted to the second portion has a viewable region 90 facing away from the second portion, as shown in FIGS. 6 and 7.

The step of mounting the case 20 to the human transport comprises attaching a hanger, which is attached near a second case end opposite the first case end, to some part of the human transport, such as a gurney, an IV pole, or the wall of an ambulance. The part of the human transport to which the case is mounted may be a pole attached to the gurney, a portion of the litter frame, a hook mounted to the wall in an ambulance or any other structure found in medical emergency or medical transport environments. The hanger of the case 20 may be the loop 30 mounted on the case 20, the clamp 34 and/or the clamp 36 mounted on the case 20, and/or the combination. The hanger could be any other structure that permits the case to be mounted to the human transport. The case may have a hook or other structure that readily hangs on another hook, a peg, a pole, or a similar structure on the human transport. Many such structures will become apparent to the person having ordinary skill from this disclosure. Any hanging structure that does not require a separate tool may be used with the invention instead of the hanger structures shown and described herein. The hanger must be able to hang the apparatus without the need for tools. Some examples of such structures are described in the following, but this list is not intended to be exhaustive. The apparatus may use snaps, VELCRO brand hooks and loops fasteners, buttons, magnets, temporary adhesive (as used with adhesive note paper), as well as any specialized fasteners that permit hanging of the case without tools. Such specialized fasteners are unlikely to be readily available on human transport devices, and therefore are less desirable than common hanging structures. However, these may become readily available, and therefore are contemplated.

Once the case is mounted to the human transport, the first portion of the case is preferably moved from the closed configuration and disposed beneath the second portion and the video display screen. This may be performed by unzipping the zipper fastener that attaches the first portion to the second portion, thereby permitting the first portion to pivot about the first case end. The first portion is pivoted down in order to operate the communication apparatus to permit the first party to view "live" the video taken of the second party that is transmitted to the viewable portion of the video display screen that is no longer obstructed by the first portion. This viewing of the viewable portion occurs at the same time that the case is mounted to the human transport, the first portion is disposed beneath the second portion and the video display screen, and the first party is captured by video that is transmitted to the second party.

Figure 13:
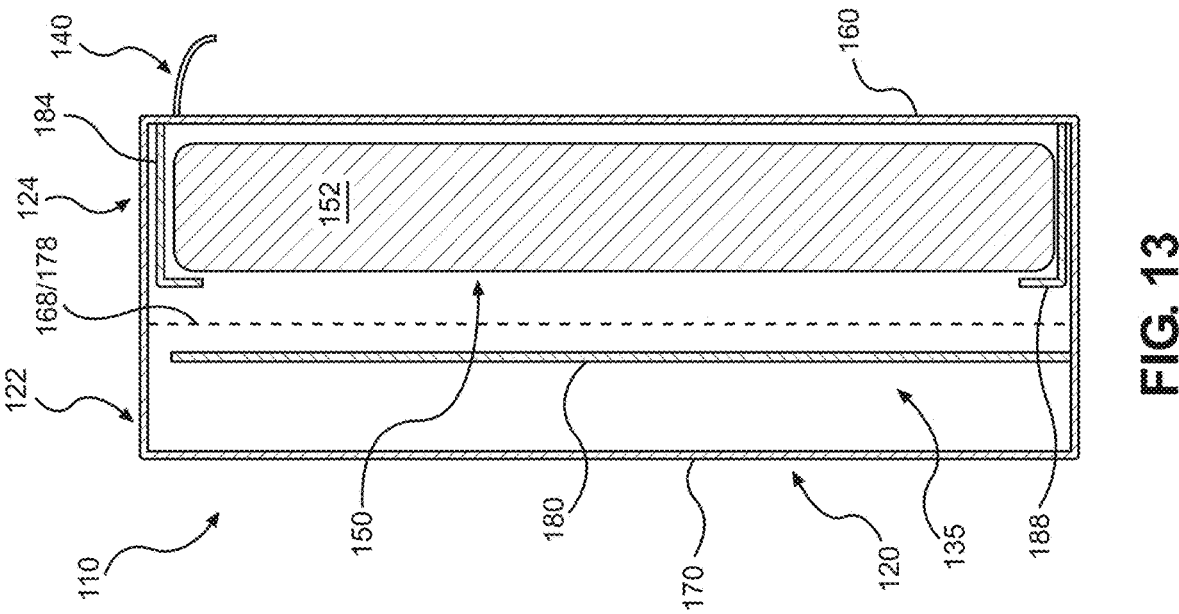
FIG. 13 is schematic side view in section illustrating the embodiment shown in FIG. 12 through the line A-A.
Figure 12:
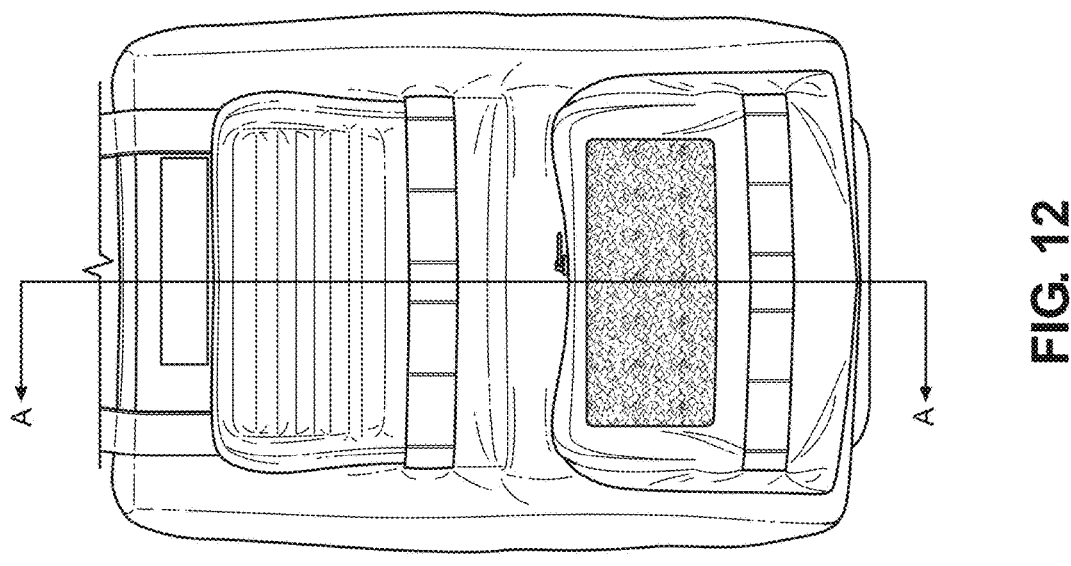
FIG. 12 is an alternative embodiment of the present invention.

An alternative embodiment is shown in FIG. 12 and is shown as a schematic side view in section in FIG. 13. This embodiment illustrates the relationship between the case's 120 first portion 122 and second portion 124 relative to the video display screen 150 of the tablet computer 152. While the video display screen 150 is perpendicular to the plane of the illustration, and is therefore not visible, the reference numeral 150 points to the front of the tablet computer 152 in the orientation of FIG. 13. The adjoined zipper teeth 168/178 are shown by a dashed line that separates the first portion 122 from the second portion 124. The braces 184 and 188 extend around from attachment to the panel 160 in the rear and restrain the tablet computer 152 by extending over the front of the frame of the tablet computer 152.

A planar panel 180 is mounted to the first portion 122 and extends between the panel 170 of the first portion and the display screen 150 of the tablet computer 152. The panel 180 is about the length and width of the display screen 150 and is advantageously made of a lightweight, rigid material. The panel 180 thereby protects the display screen 150 from contact by any instruments that might be in the chamber 135. The panel 180 may also have a surface on which indicia are printed that assist a user in operating the apparatus 110. These indicia are visible when the case 120 is in the opened configuration and the panel 180 is pivoted downwardly with the first portion 122 after opening the case 120.

Figures 28, 29:
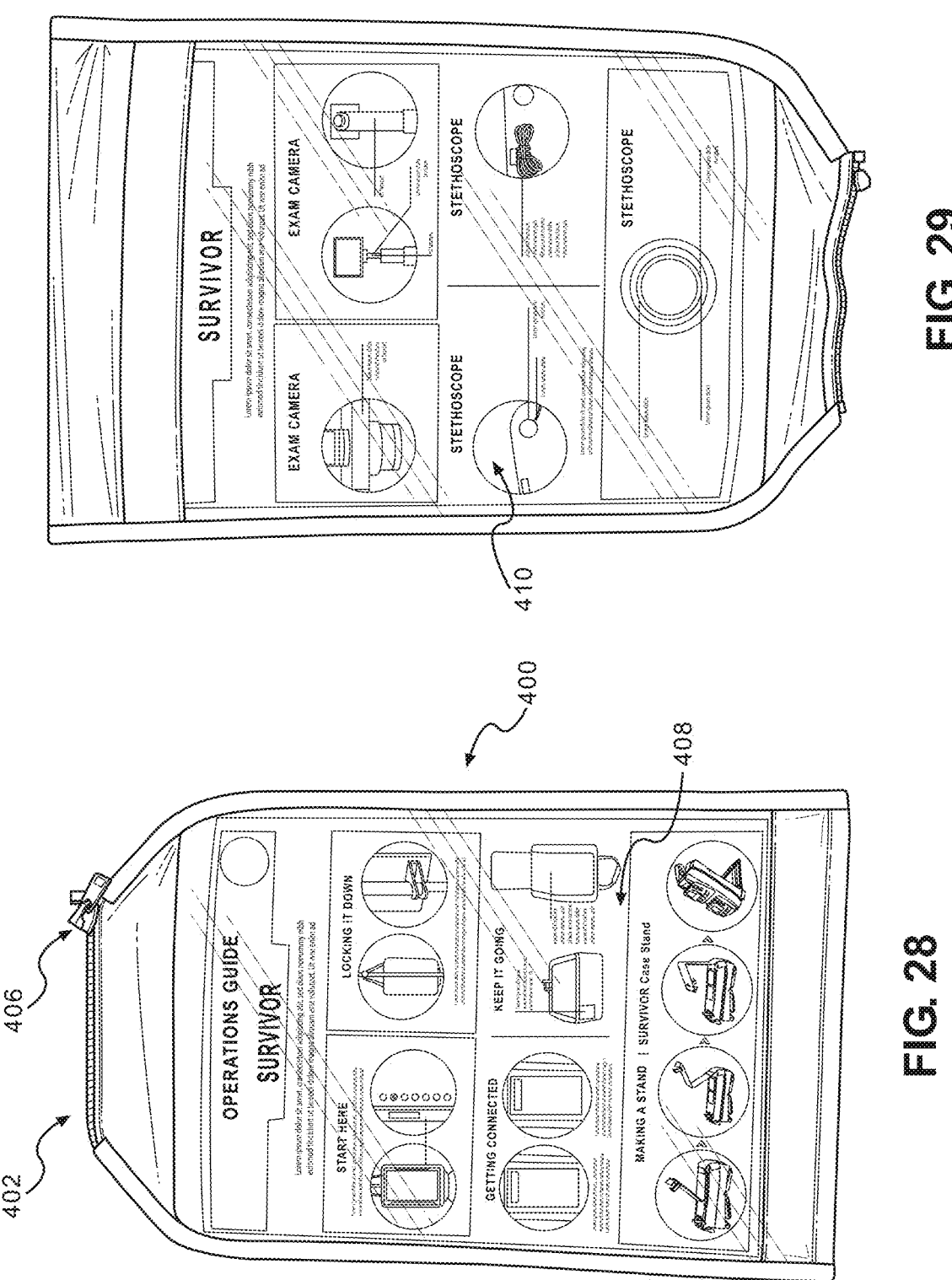
FIG. 28 is a front view illustrating an optional planar panel.
FIG. 29 is a rear view illustrating the planar panel of FIG. 28.
Figure 30:
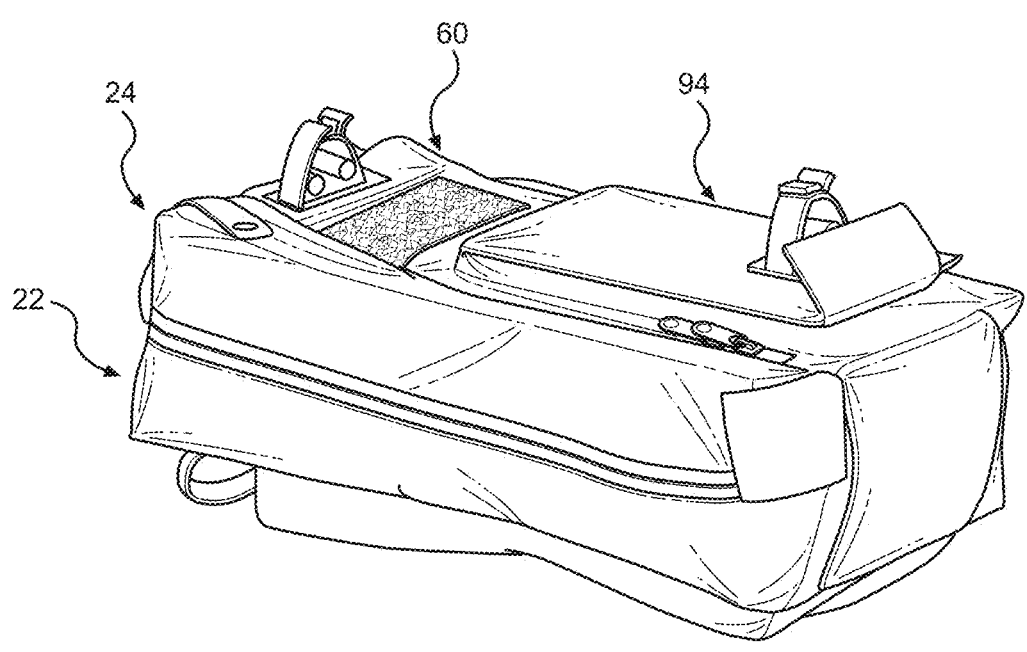
FIG. 30 is a view in perspective illustrating an embodiment of the present invention with the stand in a collapsed state.

The planar panel 400 shown in FIGS. 28 and 29 is similar to the planar panel 180, and has a fastener, such as zipper teeth 402, at one end. The zipper teeth 402 are configured to mount to a fastener, such as complementary zipper teeth 404, on the end of the panel 28 (see FIG. 8). The slider 406 can be moved manually in a conventional manner to attach the teeth 402 to the teeth 404. Thus, the planar panel 400 can be mounted to an end of the panel 28 to be disposed between the portion 22 and the portion 24 in the closed configuration. In a preferred embodiment, the planar panel 400 has a first major surface 408 and a second, opposite major surface 410, each of which has indicia printed thereon. For example, instructions for use, attachment, detachment or any other function of the instruments can be printed on one surface 410, such as when the planar panel 400 is disposed over the video screen 50 and above from the instruments. Instructions for the operation of the tablet computer 52 may be printed on the surface 408, which would be visible to the user when the planar panel 400 is placed over the instruments (typically when the case 20 is in the opened configuration). When the case 20 is in the closed configuration, as shown in FIGS. 1-5, the planar panel 400 is desirably disposed between the instruments and the tablet computer 52, thereby protecting the tablet computer's video display 50 from impacts from, or even the weight of, the instruments. When the case 20 is in the opened configuration, the planar panel 400 is used for instructions or is removed.

The planar panel 400 is preferably manufactured using the same kind of material as the panel 28, combined with clear shielded panels to form a pocket for operating instructions, which may be on a card or piece of paper. The planar panel 400 protects the video screen 50 from damage during storage and transporting. While in the open position, the planar panel 400 hangs down to expose the front side of the instructions. When the medical instruments are required, the panel flips up and the back side panel is displayed. The planar panel 400 may be removed while operating the tablet computer 52 or medical instruments. Thus, the planar panel 400 serves both as a source for instructions and a layer of cushion between the top and bottom for protection.

The communication components of the described transceivers are designed to work with the communication systems of all medical systems, military branches, first responders and commercial carriers. The described apparatus is durable and simple to use, possibly using commercial operating systems that patients and medical personnel are already familiar with, including iOS, Android and Windows brand operating systems. The transceivers may operate using the public cellular phone system, which is advantageous, but may be designed to operate over a secure communication network.

One example of the use of the invention is to send medical personnel with an embodiment of the invention to the home of a patient with ongoing chronic symptoms, and connecting the apparatus to another similar apparatus in the location of a doctor. The apparatus is readily carried by hand, and can be grasped by the medical person's hand through the loops 30 and 32 and carried in the manner of a briefcase or medical bag. The apparatus preferably has a total weight of about 13 lbs., and preferably up to a maximum of about 50 lbs. It is anticipated that the apparatus may weight 15 lbs., 20 lbs., 25 lbs., 30 lbs., 35 lbs., 40 lbs., 45 lbs., or 50 lbs. With the apparatus, medical personnel who are with the patient in a first location can connect visually and audibly to a remotely-located doctor who has similar equipment in his or her presence. The doctor faces the nearby apparatus and speaks and acts, all while audio and video of the doctor are taken by the camera and microphone, and the audio and video data are transmitted to the patient's apparatus. The patient and/or medical personnel with the patient face the nearby apparatus and speak, all while audio and video of them are taken by the camera and microphone, and the audio and video data are transmitted to the doctor's apparatus. Communication of data occurs electronically so that the patient does not have to be transported, for example, to a hospital for examination. This could work in any condition in which a doctor is not physically present with the patient, such as when the two are in different states, different cities or different buildings. Therefore a purpose of the apparatus is to be used while in flight, particularly flights that are for medical rescue purposes or other transportation environments for patients. Because the apparatus is secured to a litter or other device for transporting a patient, there is a very low probability that the apparatus could move substantially during flight and become a dangerous projectile. Furthermore, the communication protocols require low bandwidth to transmit sufficient data to operate. Finally, the apparatus uses tactical audio so that it can be connected to a conventional communication system in aircraft and emergency vehicles.

Another example of the use of the apparatus is a military situation in which a wounded soldier can be "seen" virtually by a medical specialist far away while in the local care of a general doctor, nurse or medic. A first apparatus may be located on an airplane on which the patient is being transported, such as on a pole of a litter, and another apparatus may be located at a remote location where the specialist is located.

In some embodiments, there is an instrument that attaches to the tablet computer and permits the local person (e.g., medic) to follow instructions given through the audio and video by the remote physician. For example, the physician may instruct the medic to insert the camera 82 into the patient's mouth to view the patient's throat. The video taken from the camera is transmitted, such as a window-in-a-window on the display, so the physician may see what the camera in the patient's through views, while also still viewing the patient using the main camera of the tablet computer. It is contemplated that the physician may remotely control the camera to zoom in, take still photos and videos, etc. One example of such a camera is a Jedmed horns scope camera (https://www.jedmed.com/products/hd-digital-scope-system) that has various camera lenses to permit the user to do an otoscope (a tool which shines a beam of light to help visualize and examine the condition of the ear canal and eardrum), dermscope, dental lens, or any other conventional view.

The portability of the apparatus is an important feature, and the fact that the apparatus can be used while it and the patient are being transported is a combination unknown in the prior art. The fact that the apparatus and the patient can be moved by an automobile, boat, airplane, helicopter or virtually any other vehicle while in use is an advantage. In some embodiments, the apparatus's transceiver is a low bandwidth cellular telephone, which allows the apparatus to be mobile and need no external power source while still transmitting and receiving all data needed for operation. Further, the ability to securely affix the apparatus to something in a vehicle or on a litter or gurney prevents damage (to the apparatus and surrounding objects) and permits use while moving. When attached to a litter, the device can be used when the patient is first placed on the litter, during any transport of the litter by a vehicle, when the patient arrives at a hospital or other setting and the patient is moved from the vehicle to the setting. The above-described apparatus may be in operation the entire time without interruption.

Prior art telemedicine devices that are lightweight enough to be moved by hand cannot be readily affixed to a human transport or in a vehicle, and even if they can, they cannot be used while the vehicle is moving. Therefore, some advantages of the described telemedicine apparatus include, but are not limited to, that it is mobile during its use, it uses very little bandwidth to transfer data and it may readily be affixed to a common structure in medical environments to prevent the apparatus from being harmed or harming others or property. The fact that the apparatus can record, transmit and receive audio and video data while affixed to the human transport that is moving is very advantageous.

This detailed description in connection with the drawings is intended principally as a description of the presently preferred embodiments of the invention, and is not intended to represent the only form in which the present invention may be constructed or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention and that various modifications may be adopted without departing from the invention or scope of the following claims.

The invention claimed is:

1. An improved portable communication apparatus including at least a wireless transceiver, a video display screen, a camera, a speaker and a microphone, the improvement comprising:
  (a) a case having at least a first portion and a second portion, wherein
    (i) the video display screen is mounted to the second portion with a viewable region of the video display screen facing away from the second portion;
    (ii) the first and second portions are pivotably attached to one another at a first case end;
    (iii) when the first and second portions are in a closed configuration the first and second portions form an enclosed chamber in which the video display screen is positioned with the viewable region facing toward, and obstructed by, at least the first portion;
    (iv) when the first and second portions are in an opened configuration the first portion is positioned beneath the second portion and the video display screen, and the first portion is not obstructing the viewable region; and
    (v) at least one medical examination instrument connected to the video display screen is attached to the first portion;
  (b) a hanger mounted to the second portion near a second case end that is opposite the first case end, wherein, when the case is hanging in at least the opened configuration, the second portion displays the video display screen in a direction and the first portion displays the at least one medical examination instrument in the direction so an operator has simultaneous access to the video display screen and the at least one medical examination instrument.

2. The improved portable communication apparatus in accordance with claim 1, further comprising at least one clamp attached to the second portion on a side of the second portion that is opposite the video display screen.

3. The improved portable communication apparatus in accordance with claim 2, wherein the at least one clamp further comprises a pole clamp mounted through the second portion to a bracket to which the video display screen is mounted.

4. The improved portable communication apparatus in accordance with claim 1, wherein a chamber is formed between the video display screen and the second portion of the case, wherein a wire connecting the at least one medical examination instrument to the video display screen extends into the chamber.

5. A combination human transport and a communication apparatus including at least a wireless transceiver, a video display screen, a camera, a speaker and a microphone, the combination comprising:

(a) a case having at least a first portion and a second portion, wherein
    (i) the video display screen is mounted to the second portion with a viewable region of the video display screen facing away from the second portion;
    (ii) the first and second portions are pivotably attached to one another at a location beneath the video display screenat; and
    (iii) the first portion is positioned beneath the second portion and the video display screen;
  (b) the second portion is mounted to the human transport; and
  (c) at least one medical examination instrument connected to the video display screen is attached to the first portion;
  wherein the second portion displays the video display screen in a direction and the first portion displays the at least one medical examination instrument in the direction so an operator has simultaneous access to the video display screen and the at least one medical examination instrument.

6. The combination in accordance with claim 5, further comprising at least one clamp mounted to the second portion on a side of the second portion that is opposite the video display screen, wherein the at least one clamp is attached to the second portion and the human transport.

7. The combination in accordance with claim 5, wherein the at least one clamp further comprises a pole clamp mounted through the second portion to a bracket to which the video display screen is mounted.

8. The combination in accordance with claim 7, wherein a chamber is formed between the video display screen and the second portion of the case, wherein a wire connecting the at least one medical examination instrument to the video display screen extends into the chamber.

9. A combination human transport and a communication apparatus including at least a wireless transceiver, a video display screen, a camera, a speaker and a microphone, the combination comprising:
  (a) a case having at least a first portion and a second portion, wherein
    (i) the video display screen is mounted to the second portion with a viewable region of the video display screen facing away from the second portion, and the viewable region of the video display screen is substantially greater in length in a vertical direction than in a horizontal direction;
    (ii) the first and second portions are pivotably attached to one another at a location beneath the video display screen; and
    (iii) the first portion is positioned beneath the second portion and the video display screen;
  (b) the second portion mounts to the human transport in a manner that permits ready removal.

10. The combination in accordance with claim 9, wherein the second portion displays the video display screen in a direction and the first portion displays the at least one medical examination instrument in the direction so an operator has simultaneous access to the video display screen and the at least one medical examination instrument.

11. The combination in accordance with claim 10, further comprising at least one medical examination instrument connected to the video display screen that is attached to the first portion.

12. The combination in accordance with claim 11, further comprising at least one name strip removably fastened to the first portion, the at least one name strip facing away from the first portion and including indicia communicating the type of medical examination equipment that is disposed nearby.

13. The combination in accordance with claim 9, further comprising at least one clamp mounted to the second portion on a side of the second portion that is opposite the video display screen, wherein the at least one clamp is attached to the second portion and the human transport.

14. The combination in accordance with claim 13, wherein the at least one clamp further comprises a pole clamp mounted through the second portion to a bracket to which the video display screen is mounted.

15. The combination in accordance with claim 9, wherein a chamber is formed between the video display screen and the second portion of the case, wherein a wire connecting the at least one medical examination instrument to the video display screen extends into the chamber.

16. The combination in accordance with claim 9, wherein the second portion mounts to the human transport by a flexible loop mounted to the top of the second portion of the case and extending over a hook mounted to the human transport.

* * * * *